US 12,274,757 B2

United States Patent
Lucas et al.

(10) Patent No.: US 12,274,757 B2
(45) Date of Patent: Apr. 15, 2025

(54) RECOMBINANT ADENO-ASSOCIATED VIRUSES ENCODING SERPIN PEPTIDES AND USES THEREOF

(71) Applicant: University of Florida Research Foundation, Incorporated, Gainesville, FL (US)

(72) Inventors: Alexandra Rose Lucas, Tempe, AZ (US); Alfred S. Lewin, Gainesville, FL (US); Cristhian J. Ildefonso, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1255 days.

(21) Appl. No.: 16/978,800

(22) PCT Filed: Mar. 8, 2019

(86) PCT No.: PCT/US2019/021340
§ 371 (c)(1),
(2) Date: Sep. 8, 2020

(87) PCT Pub. No.: WO2019/021340
PCT Pub. Date: Sep. 12, 2019

(65) Prior Publication Data
US 2021/0000973 A1  Jan. 7, 2021

Related U.S. Application Data

(60) Provisional application No. 62/640,599, filed on Mar. 9, 2018.

(51) Int. Cl.
| | |
|---|---|
| A61K 48/00 | (2006.01) |
| A61P 27/02 | (2006.01) |
| A61P 29/00 | (2006.01) |
| A61P 37/06 | (2006.01) |
| C07K 14/81 | (2006.01) |
| C12N 15/86 | (2006.01) |

(52) U.S. Cl.
CPC ........ *A61K 48/005* (2013.01); *A61K 48/0075* (2013.01); *A61P 27/02* (2018.01); *A61P 29/00* (2018.01); *A61P 37/06* (2018.01); *C07K 14/81* (2013.01); *C12N 15/86* (2013.01); *C12N 2750/14123* (2013.01); *C12N 2750/14143* (2013.01)

(58) Field of Classification Search
CPC ... A61K 48/005; A61K 48/0075; A61P 27/02; A61P 29/00; A61P 37/06; C07K 14/81; C07K 14/8132; C07K 2319/50; C07K 2319/60; C07K 14/005; C07K 14/811; C12N 15/86; C12N 2750/14123; C12N 2750/14143; C12N 2710/24022; A01K 2217/075; A01K 2227/105; A01K 2267/0368
See application file for complete search history.

(56) References Cited

U.S. PATENT DOCUMENTS

| | | | |
|---|---|---|---|
| 6,391,858 B2 | 5/2002 | Podsakoff et al. | |
| 7,745,396 B2 | 6/2010 | Lucas | |
| 9,226,976 B2 * | 1/2016 | Flotte | C12N 7/00 |
| 2016/0038576 A1 * | 2/2016 | Vasserot | C07K 16/28 |
| | | | 435/69.3 |

OTHER PUBLICATIONS

Tse, L.V., 2017. Structure-guided evolution of antigenically distinct adeno-associated virus variants for immune evasion. Proceedings of the National Academy of Sciences, 114(24), pp. E4812-E4821. (Year: 2017).*
Sharma, A., Ghosh, A., Hansen, E.T., Newman, J.M. and Mohan, R.R., 2010. Transduction efficiency of AAV 2/6, 2/8 and 2/9 vectors for delivering genes in human corneal fibroblasts. Brain research bulletin, 81(2-3), pp. 273-278. (Year: 2010).*
Lisowski, L., Dane, A., Chu, K. et al. Selection and evaluation of clinically relevant AAV variants in a xenograft liver model. Nature 506, 382-386 (2014). https://doi.org/10.1038/nature12875 (Year: 2014).*
Beltran, W.A., Boye, S.L., Boye, S.E., Chiodo, V.A., Lewin, A.S., Hauswirth, W.W. and Aguirre, G.D., 2010. rAAV2/5 gene-targeting to rods: dose-dependent efficiency and complications associated with different promoters. Gene therapy, 17(9), pp. 1162-1174. (Year: 2010).*
International Search Report and Written Opinion mailed May 31, 2019 in connection with Application No. PCT/US2019/021340.
International Preliminary Report on Patentability mailed Sep. 24, 2020 in connection with Application No. PCT/US2019/021340.
[No Author Listed] SERPINE1 Adenovirus. SignaGen Laboratories, Product 18529/23338. Retrieved from the Internet <http://signagen.com/index.php?main_page=product_music_info&products_id=32096>. Jun. 8, 2011. 1 page.
PCT/US2019/021340, May 31, 2019, International Search Report and Written Opinion.
PCT/US2019/021340, Sep. 24, 2020, International Preliminary Report on Patentability.

* cited by examiner

*Primary Examiner* — Jeremy C Flinders
*Assistant Examiner* — Masudur Rahman
(74) *Attorney, Agent, or Firm* — Wolf, Greenfield & Sacks, P.C.

(57) ABSTRACT

In some aspects, the disclosure relates to compositions and methods that are useful for treating inflammatory disorders and conditions. In some embodiments, the disclosure provides recombinant adeno-associated virus (rAAV) vectors and particles encoding a transgene that expresses a Myxomavirus serine proteinase inhibitor (Serp) protein (e.g., Serp-1) and methods for treating inflammatory disorders using the same.

15 Claims, 8 Drawing Sheets
Specification includes a Sequence Listing.

RECOMBINANT ADENO-ASSOCIATED VIRUSES ENCODING SERPIN PEPTIDES AND USES THEREOF

RELATED APPLICATIONS

This application is a national stage filing under 35 U.S.C. § 371 of international PCT application, PCT/US2019/021340, filed Mar. 8, 2019, which claims priority under 35 U.S.C. § 119(e) to U.S. provisional patent application, U.S. Ser. No. 62/640,599, filed Mar. 9, 2018, the entire contents of each of which are incorporated herein by reference.

BACKGROUND

Myxomavirus Serp-1 is a secreted, heavily glycosylated 55 kDa protein that contains 369 amino acid residues and belongs to the serpin superfamily. As such, Serp-1 shares ~30% sequence homology with other serpins, indicating a similar mode of function. The general mechanism of serpin function occurs through a suicide inhibitory interaction between residues of the Reactive Center Loop (RCL; residues 305-331) and targeted proteases. Through the RCL, Serp-1 can target thrombolytic proteinases, tissue- and urokinase-type plasminogen activators (tPA and uPA, respectively), plasmin, factor Xa, and thrombin in regulation of coagulation. Serp-1 shares some protease targets with the human serpin plasminogen activator inhibitor-1 (PAI-1, SERPINE1), which is the dominant mammalian inhibitor of tPA and uPA and can also inhibit activated protein C and thrombin in the presence of the glycosaminoglycan heparin sulfate, in addition to targets of anti-thrombin (ATIII, SERPINC1).

SUMMARY

Aspects of the disclosure relate to compositions and methods that are useful for inhibiting serine proteinases, for example human serpins. The disclosure is based, in part, on recombinant adeno-associated virus (rAAV) vectors and particles configured to express Myxoma virus serine proteinase inhibitor 1 (Serp-1). In some embodiments, rAAV vectors and particles described by the disclosure express one or more transgenes that inhibit certain human serine proteinase enzymes (e.g., PAI-1, ATIII, A1AT etc.) and are therefore useful for treating certain inflammatory diseases such as macular degeneration, uveitis, hemorrhagic vascular disease, inflammatory vasculitis, transplant vasculitis, lupus, lung hemorrhage, diffuse alveolar hemorrhage, transplant rejection, ischemia reperfusion, etc.

Accordingly, in some aspects, the disclosure provides a recombinant adeno-associated virus (rAAV) vector comprising an isolated nucleic acid encoding a Serp-1 peptide or a portion thereof flanked by two adeno-associated virus (AAV) inverted terminal repeat (ITR) sequences.

In some embodiments, a Serp-1 peptide or portion thereof is encoded by an amino acid sequence that is at least 90% identical a sequence set forth in SEQ ID NO: 1.

In some embodiments, a portion of a Serp-1 peptide comprises a reactive center loop (RCL) region. In some embodiments, a portion of a Serp-1 peptide comprises amino acid residues 305-331 of SEQ ID NO: 1.

In some embodiments, an isolated nucleic acid encodes a Serp-1 peptide comprising or consisting of the amino acid sequence set forth in SEQ ID NO: 1.

In some embodiments, an rAAV vector described by the disclosure comprises AAV2 ITRs.

In some embodiments, an isolated nucleic acid (e.g., an rAAV vector) comprises a promoter operably linked to a sequence encoding a Serp-1 peptide or portion thereof. In some embodiments, a promoter is a chicken beta-actin (CBA) promoter or a CAG promoter.

In some embodiments, an isolated nucleic acid (e.g., an rAAV vector) comprises a linker sequence. In some embodiments, a linker sequence is a cleavable linker sequence. In some embodiments, a cleavable linker sequence is a P2A self-cleaving linker sequence.

In some embodiments, an isolated nucleic acid (e.g., an rAAV vector) further comprises a sequence encoding a detectable marker. In some embodiments, a detectable marker is a GFP protein.

In some embodiments, an isolated nucleic acid sequence (e.g., an rAAV vector) is located on a plasmid.

In some embodiments, an rAAV vector comprises a nucleic acid sequence set forth in any one of SEQ ID NOs: 2-4.

In some aspects, the disclosure provides a recombinant adeno-associated virus (rAAV) particle comprising: an rAAV vector as described by the disclosure; and one or more adeno-associated virus (AAV) capsid proteins.

In some embodiments, one or more AAV capsid proteins is of a serotype selected from serotype 2, 3, 4, 5, 6, 7, 8, 9, 10, and variants thereof. In some embodiments, one or more AAV capsid proteins is of an AAV2 serotype or a variant thereof. In some embodiments, an AAV2 serotype variant is an AAV2 Quad+T-V variant.

In some aspects, the disclosure provides a composition comprising an isolated nucleic acid as described by the disclosure, or an rAAV as described by the disclosure, and a pharmaceutically acceptable excipient.

In some aspects, the disclosure provides a host cell comprising an isolated nucleic acid of as described by the disclosure, or an rAAV as described by the disclosure. In some embodiments, a host cell is a bacterial cell, a mammalian cell, or an insect cell. In some embodiments, a mammalian cell is a HEK293. In some embodiments, an insect cell is an Sf9 cell.

In some aspects, the disclosure provides a method for treating an inflammatory disorder in a subject, the method comprising administering an isolated nucleic acid as described by the disclosure, an rAAV as described by the disclosure, or a composition as described by the disclosure to a subject having or suspected of having an inflammatory disorder.

In some embodiments, an inflammatory disorder is macular degeneration, uveitis, hemorrhagic vascular disease, inflammatory vasculitis, transplant vasculitis, lupus, lung hemorrhage, diffuse alveolar hemorrhage, transplant rejection, or ischemia reperfusion.

In some embodiments, an inflammatory disorder affects the eye of a subject, for example macular degeneration or uveitis. In some embodiments, an isolated nucleic acid, rAAV, or composition is administered to the eye of a subject. In some embodiments, the administration comprises intraocular injection, intravitreal injection, or topical administration.

In some embodiments, an inflammatory disorder affects the lungs of a subject, for example lupus, lung hemorrhage, or diffuse alveolar hemorrhage. In some embodiments, an isolated nucleic acid, rAAV, or composition is administered to the lung of a subject. In some embodiments, the administration comprises intravenous injection, intranasal administration, or oral administration (e.g., via inhaler).

In some embodiments, an inflammatory disorder affects the heart of a subject, for example ischemia reperfusion (e.g., ischemia reperfusion after acute myocardial infarction). In some embodiments, an isolated nucleic acid, rAAV, or composition is administered to the heart of a subject. In some embodiments, the administration comprises intravenous injection, myocardial injection, or coronary artery perfusion.

In some embodiments, an inflammatory disorder affects the blood vessels of a subject, for example hemorrhagic vascular disease, inflammatory vasculitis, or transplant vasculitis. In some embodiments, an isolated nucleic acid, rAAV, or composition is administered systemically to a subject. In some embodiments, the administration comprises intravenous injection.

In some embodiments, an inflammatory disorder is transplant rejection. In some embodiments, an isolated nucleic acid, rAAV, or composition is administered to a transplant site of a subject.

In some aspects, the disclosure provides a method of delivering a transgene to the eye of a subject, the method comprising administering an isolated nucleic acid as described by the disclosure, or an rAAV as described by the disclosure, or a composition as described by the disclosure, to a subject.

In some embodiments, a subject is a mammal. In some embodiments, a subject is a human.

In some embodiments, administration of an isolated nucleic acid, rAAV, or composition as described herein results in expression of the transgene in the eye of a subject.

DETAILED DESCRIPTION

Figure 1:
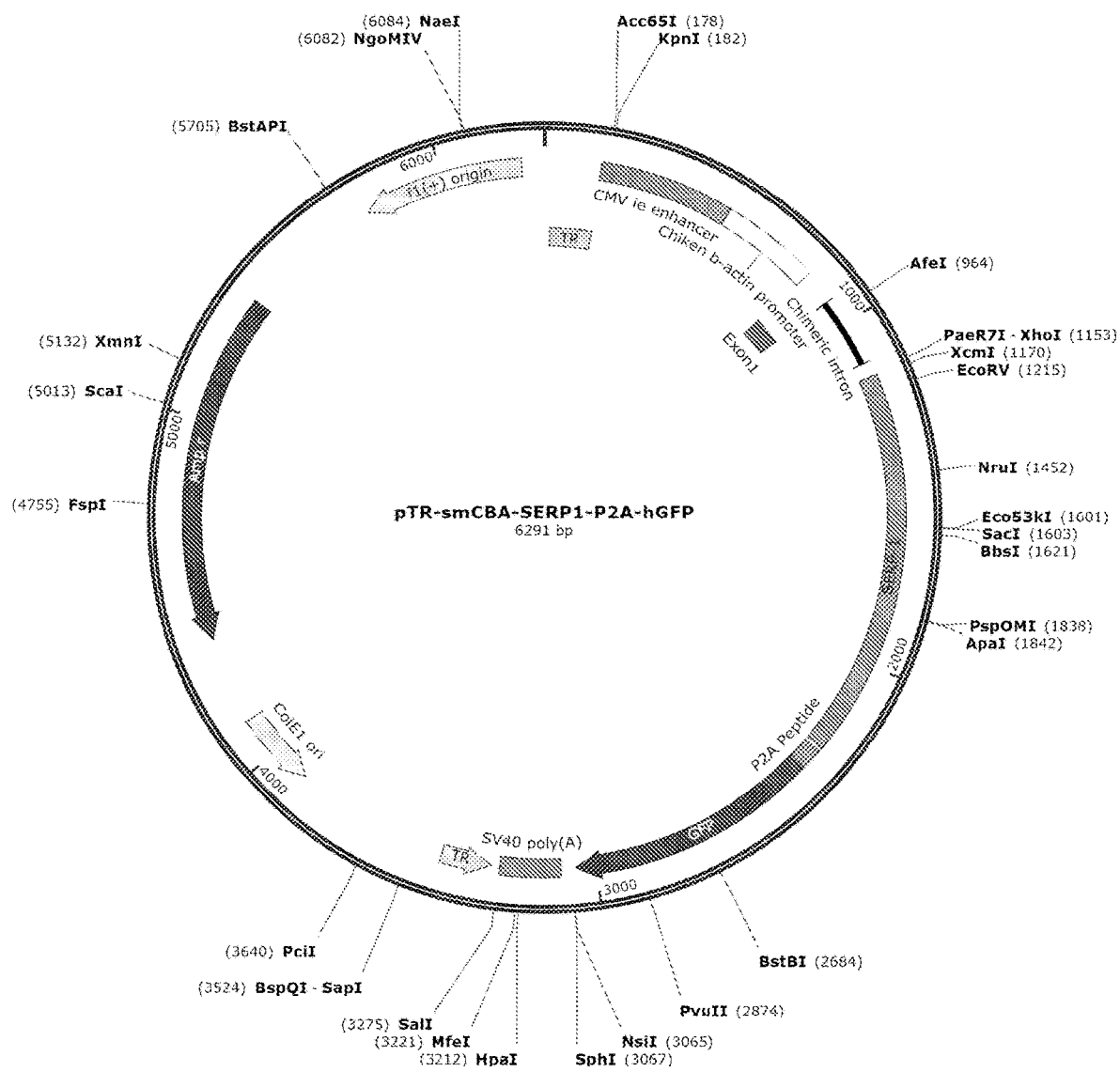
FIG. 1 shows a schematic vector map depicting one embodiment of an rAAV vector comprising AAV2 inverted terminal repeat (ITR) sequences flanking an expression cassette comprising a transgene encoding a Serp-1 peptide. In this embodiment, the expression cassette further comprises a P2A self-cleaving peptide and a GFP marker.

The disclosure relates, in some aspects, to compositions and methods useful for reducing inflammation in a target tissue (e.g., eye, lung, heart, skin, etc.). The disclosure is based, in part, on compositions (e.g., recombinant adeno-associated virus (rAAV) vectors, rAAV particles, etc.) comprising certain virally-derived peptides, such as a Serp-1 peptide or a portion thereof, that inhibit certain human serine proteinase enzymes (e.g., PAI-1, ATIII, A1AT etc.) and are therefore useful for treating certain inflammatory diseases.

Accordingly, in some aspects, the disclosure provides a recombinant adeno-associated virus (rAAV) vector comprising an isolated nucleic acid encoding a Serp-1 peptide or a portion thereof flanked by two adeno-associated virus (AAV) inverted terminal repeat (ITR) sequences.

Serpins

In some aspects, the disclosure relates to isolated nucleic acids (e.g., rAAV vectors) encoding a serpin peptide or a portion thereof. Serpin peptides are serine protease inhibitors that are typically derived from viruses from the genus *Leporipoxvirus*, which have been observed to cause the disease myxomatosis in rabbits. In mammals, certain serpin peptides have been observed to modulate clot formation, immune responses, apoptosis and other biological processes. In some embodiments, an isolated nucleic acid as described by the disclosure encodes a serpin peptide derived from a Myxoma virus. Examples of Myxoma virus serpins include but are not limited to Serp-1 and Serp-2. In some embodiments, an isolated nucleic acid as described herein encodes a Serp-1 peptide or a portion thereof. In some embodiments, a Serp-1 peptide is represented by the nucleic acid sequence set forth in NCBI Gene ID: 932201. In some embodiments, a Serp-1 peptide is represented by the amino acid sequence set forth in NCBI Reference Sequence: NP_051722.1.

In some embodiments, an isolated nucleic acid described by the disclosure encodes a Serp-1 peptide variant. For example, in some embodiments, a Serp-1 peptide variant comprises an amino acid sequence that is at least 70%, at least 80%, at least 90%, at least 95%, or at least 99% (e.g., any percentage between 70% and 99% inclusive) identical to the amino acid sequence set forth in SEQ ID NO: 1. In some embodiments, a Serp-1 peptide variant comprises an amino acid sequence that is at least 70%, at least 80%, at least 90%, at least 95%, or at least 99% (e.g., any percentage between 70% and 99% inclusive) identical to the nucleic acid sequence set forth in NCBI Gene ID: 932201. In some embodiments, a Serp-1 peptide variant is a codon-optimized variant of a Myxoma virus Serp-1 peptide. Codon optimization is well-known in the art and is described, for example by Quax et al. (2015) *Molecular Cell* 59:149-161.

In some embodiments, an isolated nucleic acid as described by the disclosure encodes a portion of a serpin peptide, for example a portion of a Serp-1 peptide. A "portion" of a protein refers to a truncated amino acid sequence that retains the intended function of the full-length protein from which it is derived. A portion of a protein can be truncated at the N-terminus, C-terminus, or N- and C-termini relative to the protein from which the portion is derived. In some embodiments, a portion of a protein comprises an amino acid sequence comprising at least 20%, at least 30%, at least 40%, at least 50%, at least 60%, at least 70%, at least 80%, at least 90%, at least 95%, or at least 99% of the amino acids present in the protein from which the portion is derived.

In the context of serpin peptides, a portion of a serpin peptide (e.g., Serp-1) comprises an amino acid sequence that is truncated (e.g., shortened) relative to a full-length amino acid sequence of a Serp-1 peptide, for example SEQ ID NO: 1, and maintains the ability to inhibit tissue- and urokinase-type plasminogen activators (e.g., tPA and uPA, respectively), or inhibit plasmin in the thrombolytic cascade, and/or inhibit factor Xa (fXa) in the thrombotic cascade. In some embodiments, a portion of a serpin peptide (e.g., a portion of Serp-1) comprises between 1 and 100 (e.g., any integer between 1 and 100, inclusive) fewer amino acids than SEQ ID NO: 1. In some embodiments, a portion of a serpin peptide or serpin peptide variant comprises a reactive center loop (RCL) region. Generally, the RCL of serpin mediates a suicide inhibitory interaction between residues of the Reactive Center Loop (RCL; e.g., residues 305-331 of SEQ ID NO: 1) and targeted proteases. Serpin RCL peptides are generally described, for example by Ambadapadi et al. (2016) *J. Biol Chem* 291(6):2874-2887.

Recombinant Adeno-Associated Virus (rAAV) Vectors

In some aspects, the disclosure relates to recombinant adeno-associated virus (rAAV) vectors. Generally, "rAAV vector" refers to an isolated nucleic acid sequence comprising an expression cassette engineered to express a transgene of interest (e.g., a Serp-1 peptide or a portion thereof), that is flanked by two adeno-associated virus (AAV) inverted terminal repeat (ITR) sequences.

The ITR sequences can be derived from any AAV serotype, including but not limited to AAV2, AAV3, AAV4, AAV5, AAV6, AAV7, AAV8, AAV9. In some embodiments, the AAV ITR sequences are AAV2 ITR sequences. In some embodiments, one of the ITR sequences in a rAAV vector is a truncated ITR (e.g., a ΔTRS ITR), which in some embodiments are useful for production of self-complementary rAAVs (scAAVs). In some embodiments, an rAAV vector is part of a plasmid (e.g., a bacterial plasmid).

In some embodiments, an expression cassette of an rAAV vector comprises one or more control elements (also referred to as regulatory sequences) that allow for regulation of gene expression, for example Serp-1 peptide expression. Non-limiting examples of control elements include promoters, insulators, silencers, response elements, introns, enhancers, initiation sites, termination signals, and poly(A) tails. Any combination of such control sequences is contemplated herein (e.g., a promoter and an enhancer).

In some embodiments, one or more promoters may be operably linked to a coding nucleotide sequence in the heterologous nucleic acid. A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter.

For example, constitutive promoters of different strengths can be used. A nucleic acid described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. In some embodiments, chimeric viral/mammalian promoters may include a chimeric CMV/chicken beta actin (CBA, CB or CAG) promoters.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. In some embodiments, it may be beneficial to combine an isolated nucleic acid (e.g., an isolated nucleic acid encoding Serp-1 peptide or a portion thereof) as disclosed herein, with a promoter that targets the cells, tissue, or organ where expression of Serp-1 is desired. For example, if Sertp-1 expression is desired in the eye of a subject, a nucleic acid may comprise a promoter that targets photoreceptor cells or the retina as a whole. In some embodiments, a cell-type-specific promoter targeting the retina is human rhodopsin kinase promoter (hGRK1). Non-limiting examples of hGRK1 promoter can be found in Beltran et al., 2010, Gene Ther. 17:1162, Zolotukhin et al., 2005, Hum Gene Ther. 16:551, and Jacobson et al., Mol Ther. 13:1074. In some embodiments, a retina-specific promoter is a Pleiades Mini-promoter (for example Ple155). In some embodiments, a retina-specific promoter is glial fibrillary acidic protein promoter. Other non-limiting examples of promoters that can be used as retinal cell-type-specific promoters include red opsin promoter "PR2.F" (which targets M and L cones), chimeric 'IRBPe-GNAT2' promoter (which targets all cones), IRBP promoter (which targets rods), Grm6-SV40 enhancer/promoter (which targets bipolar cells), Thy1 (which targets RGCs), other Pleiades promoters, rod opsin promoter (which targets rods), cone arrestin promoters (which targets all cones), VMD2 or Bestrophin promoter (which targets RPE cells).

Several promoters are publically available or described. For example, Ple155 promoter is available through Addgene plasmid repository (Addgene plasmid #29011, addgene.org/29011/) and is described in Scalabrino et al. (Hum Mol Genet. 2015, 24(21):6229-39). Ye et al. (Hum Gene Ther.; 27(1):72-82) describes a shorter version of this promoter called PR1.7. A Thy1 promoter construct is also available through Addgene plasmid repository (Addgene plasmid #20736, addgene.org/20736/). A GRM6 promoter construct is also available through Addgene plasmid repository (Addgene plasmid #66391, addgene.org/66391/). Guziewicz et al. (PLoS One. 2013 Oct. 15; 8(10):e75666) and Esumi et al (J Biol Chem. 2004, 279(18):19064-73) provide examples of the use of VMD2 promoter. Dyka et al. (Adv Exp Med Biol. 2014; 801: 695-701) describes cone specific promoters for use in gene therapy, including IRBP and IRBPe-GNAT2 promoter. The use of PR2.1 promoter has been demonstrated in Komáromy et al. (Gene Ther. 2008 July; 15(14):1049-55) and its characterization in Karim et al. (Tree Physiol. 2015 October; 35(10):1129-39). Aartsen et al. (PLoS One, 5(8): e12387) describes the use of GFAP promoter to drive GFP expression in Muller glial cells. Other examples of Muller glia specific promoters are RLBP1 and GLAST (Vázquez-Chona, Invest Ophthalmol Vis Sci. 2009, 50(8):3996-4003; Regan et al., Journal of Neuroscience, 2007, 27(25): 6607-6619).

In some embodiments, an isolated nucleic acid as described by the disclosure comprises a cell-type-specific promoter targeting lung tissue. Examples of lung-specific promoters include but are not limited to lung epithelial cell-specific surfactant protein B gene promoter and the Clara cell-specific promoter CC10.

In some embodiments, an isolated nucleic acid as described by the disclosure comprises a cell-type-specific promoter targeting cardiac (heart) tissue. Examples of cardiac-specific promoters include but are not limited to promoters for Myh6, MYL2 (e.g., MLC-2V), TNNI3, NPPA, Slc8a1, etc.

In some embodiments, an isolated nucleic acid as described by the disclosure comprises a cell-type-specific promoter targeting liver tissue. Examples of liver-specific promoters include but are not limited to promoters for APOA2, SERPINA1 (e.g., hAAT), CYP3A4, miR-122, etc.

Synthetic promoters are also contemplated herein. A synthetic promoter may comprise, for example, regions of known promoters, regulatory elements, transcription factor binding sites, enhancer elements, repressor elements, and the like.

It is to be understood that a promoter may be a fragment of any one of the promoters disclosed herein, or one that retains partial promoter activity (e.g., 10-90, 30-60, 50-80, 80-99 or 90-99.9% of the activity) of a whole promoter.

In some embodiments, a linker sequence encodes a peptide spacer, for example a glycine-rich and/or serine-rich peptide (e.g., GGGGS (SEQ ID NO: 7), (GGGGS)$_x$, where x is an integer between 1 and 20, etc.). The length of a linker can vary, for example from about 1 amino acid to about 500 amino acids (e.g., any integer between 1 and 500, inclusive). In some embodiments, a linker sequence comprises a cleavable linker sequence. Non-limiting examples of cleavable linkers include enzyme (e.g., protease) cleavable linkers and photocleavable linkers and are described for example in Leriche et al. (2012) *Bioorg Med Chem* 20(2):571-82. Examples of protease cleavable linkers include amino acid sequences that are substrates for cathepsin (e.g., cathepsin B), matrix metalloproteases (e.g., MMP1, MMP9, etc.), and furin. Generally, the number of protease cleavage substrates can vary. In some embodiments, a linker sequence encodes 1, 2, 3, 4, 5, 6, 7, 8, 9 or 10 protease cleavage sites.

In some embodiments, the one or more protease cleavage sites is a self-cleaving protease cleavage site. The term "self-cleaving protease cleavage site" generally refers to a peptide (e.g., an amino acid sequence encoding a peptide) that is derived from a picoronavirus and allows for multicistronic translation of non-linked peptides from an isolated nucleic acid. Examples of self-cleaving peptides include but are not limited to 2A peptides, such as P2A, E2A, T2A, F2A, etc., and are described by Kim et al. (2011) *PLoS ONE* 6(4): e18556. In some embodiments, a self-cleaving protease cleavage site is a P2A self-cleaving protease cleavage site. In some embodiments, a P2A self-cleaving protease site comprises a sequence set forth in SEQ ID NO: 5.

rAAV Particles

In some aspects, the disclosure provides recombinant AAVs (rAAVs) comprising an isolated nucleic acid as described herein.

The AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The rep ORF is composed of four overlapping genes encoding Rep proteins required for the AAV life cycle. The cap ORF contains overlapping nucleotide sequences of capsid proteins: VP1, VP2 and VP3, which interact together to form a capsid of an icosahedral symmetry.

The capsid proteins, which are controlled by the same promoter, designated p40, are translated from the same mRNA. The molecular weights of VP1, VP2 and VP3 are 87, 72 and 62 kiloDaltons, respectively. The AAV capsid is composed of 60 capsid protein subunits, VP1, VP2, and VP3, that are arranged in an icosahedral symmetry in a ratio of 1:1:10.

In some embodiments, a rAAV particle comprises a rAAV vector comprising an isolated nucleic acid as described herein flanked by ITRs of serotype 2. In some embodiments, a rAAV particle is a pseudotyped rAAV particle, which comprises (a) a capsid comprised of capsid proteins derived from a serotype other than serotype 2 (e.g., serotype 3, 4, 5, 6, 7, 8, 9, etc.), and (b) a rAAV vector comprising ITRs from serotype 2. For example, a particle may have ITRs of serotype 2 and a capsid of serotype 6. Such a pseudotyped rAAV particle would be designated AAV2/6.

In some embodiments, a rAAV particle comprises (a) a capsid comprised of capsid proteins derived from a serotype selected from serotype 2, 3, 4, 5, 6, 7, 8, 9, and 10, and (b) a rAAV vector comprising ITRs from serotype 2 flanking an expression cassette comprising an isolated nucleic acid as described herein.

Generally, a rAAV as described herein may comprise capsid proteins of any serotype (e.g., 2, 3, 4, 5, 6, 7, 8, 9, 10, and variants thereof, or certain non-human capsid protein serotypes, such as rh10, rh39, etc.). In some preferred embodiments, rAAV particles have one or more capsid proteins of serotype 2 or variants thereof. Examples of serotype 2 capsid variants are described, for example by Kay et al. (2013) *PLoS ONE* 8(4): e62097 and Boye et al. (2016) *J Virol.* 90(8):4215-31. In some embodiments, an rAAV comprises an AAV2 variant having one or more of the following mutations: Y272F, Y444F, Y500F, Y730F, and T491V. In some embodiments, an rAAV comprises an AAV2 variant having the following mutations: Y272F, Y444F, Y500F, Y730F, and T491V (also referred to as AAV2 Quad+T-V)

In some preferred embodiments, rAAV particles have one or more capsid proteins of serotype 6 or variants thereof. In some embodiments, an rAAV comprises an AAV6 variant having one or more of the following mutations: Y705F, Y731F, and T492V. In some embodiments, an rAAV comprises an AAV6 variant having the following mutations: Y705F, Y731F, and T492V (e.g., AAV6*).

Various methods of producing rAAV particles and nucleic acid vectors are known (see, e.g., Zolotukhin et al. Production and purification of serotype 1, 2, and 5 recombinant adeno-associated viral vectors. *Methods* 28 (2002) 158-167; and U.S. Patent Publication Numbers US20070015238 and US20120322861, which are incorporated herein by reference; and plasmids and kits available from ATCC and Cell Biolabs, Inc.). In some embodiments, a vector (e.g., a plasmid) comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP region as described herein), and transfected into a recombinant cells, called helper or producer cells, such that the nucleic acid vector is packaged or encapsidated inside the capsid and subsequently purified.

Non-limiting examples of mammalian helper cells include HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect helper cells is Sf9 cells (see, e.g., ATCC® CRL-1711™). A helper cell may comprises rep and/or cap genes that encode the Rep protein and/or Cap proteins. In some embodiments, the packaging is performed in vitro (e.g., outside of a cell).

In some embodiments, a nucleic acid vector (e.g., a plasmid) containing the gene of interest is combined with one or more helper plasmids, e.g., that contain a rep gene of a first serotype and a cap gene of the same serotype or a different serotype, and transfected into helper cells such that the rAAV particle is packaged. In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, *Human Gene Therapy*, Vol. 9, 2745-2760; Kern, A. et al. (2003), Identification of a Heparin-Binding Motif on Adeno-Associated Virus Type 2 Capsids, *Journal of Virology*, Vol. 77, 11072-11081.; Grimm et al. (2003), Helper Virus-Free, Optically Controllable, and Two-Plasmid-Based Production of Adeno-associated Virus Vectors of Serotypes 1 to 6, *Molecular Therapy*, Vol. 7, 839-850; Kronenberg et al. (2005), A Conformational Change in the Adeno-Associated Virus Type 2 Capsid Leads to the Exposure of Hidden VP1 N Termini, *Journal of Virology*, Vol. 79, 5296-5303; and Moullier, P. and Snyder, R. O. (2008), International efforts for recombinant adeno-associated viral vector reference standards, *Molecular Therapy*, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), *J Virology,* 6:3096-3101).

ITR sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. *Proc Natl Acad Sci USA*. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Genebank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

A non-limiting method of rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes, cap genes, and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. As an example, HEK293 cells (available from ATCC®) are transfected via CaPO4-mediated transfection, lipids or polymeric molecules such as Polyethylenimine (PEI) with the helper plasmid(s) and a plasmid containing a nucleic acid vector. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example, Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Methods for large-scale production of AAV using a herpesvirus-based system are also known. See for example, Clement et al. (*Hum Gene Ther.* 2009, 20(8):796-806). Methods of producing exosome-associated AAV, which can be more resistant to neutralizing anti-AAV antibodies, are also known (Hudry et al., *Gene Ther.* 2016, 23(4):380-92; Macguire et al., *Mol Ther.* 2012, 20(5):960-71).

Methods for producing and using pseudotyped rAAV vectors are also known in the art (see, e.g., Duan et al., J. Virol., 75:7662-7671, 2001; Halbert et al., *J. Virol.*, 74:1524-

1532, 2000; Zolotukhin et al., *Methods,* 28:158-167, 2002; and Auricchio et al., *Hum. Molec. Genet.,* 10:3075-3081, 2001).

Compositions

Various formulations have been developed to facilitate rAAV particle use. For example, for administration of an injectable aqueous solution of rAAV particles, the solution may be suitably buffered, if necessary, and the liquid diluent first rendered isotonic with sufficient saline or glucose. In some embodiments, a composition as provided herein comprises a plurality of any one of the rAAV particles disclosed herein. In some embodiments, a composition comprises pluralities of more than one of the rAAV particles disclosed herein. In some embodiments, "administering" or "administration" means providing a material to a subject in a manner that is pharmacologically useful.

Accordingly, in some embodiments, a composition of variant rAAV particles comprises a pharmaceutically acceptable carrier. The term "carrier" refers to a diluent, adjuvant, excipient, or vehicle with which the rAAV particle is administered. Such pharmaceutical carriers can be sterile liquids (e.g., water, oils, saline solutions, aqueous dextrose and glycerol solutions), suspending agents, preserving agents (e.g., methyl-, ethyl-, and propyl-hydroxy-benzoates), and pH adjusting agents (such as inorganic and organic acids and bases). In some embodiments, carriers include buffered saline solutions (e.g., phosphate buffered saline, HEPES-buffered saline). USP grade carriers and excipients are particularly useful for delivery of rAAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

In some embodiments, a composition comprising any one of the rAAV particles disclosed herein comprises Balanced Salt Solution (BSS) supplemented with 0.014% Tween 20 (polysorbate 20).

Typically, compositions may contain at least about 0.1% of the therapeutic agent (e.g., rAAV particle) or more, although the percentage of the active ingredient(s) may be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms of rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

Preparation of compositions for administration to a subject are known in the art. For example, a dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Therapeutic Methods

In some aspects, the disclosure relates to methods for delivering an isolated nucleic acid or rAAV to the eye, lung, heart, liver, or transplant site of a subject. Methods described by the disclosure are useful, in some embodiments, for the treatment of certain inflammatory disorders, for example macular degeneration, uveitis, hemorrhagic vascular disease, inflammatory vasculitis, transplant vasculitis, lupus, lung hemorrhage, diffuse alveolar hemorrhage, transplant rejection, or ischemia reperfusion.

In some aspects, the disclosure provides a method for treating an inflammatory disorder in a subject, the method comprising administering an isolated nucleic acid as described by the disclosure, an rAAV as described by the disclosure, or a composition as described by the disclosure to a subject having or suspected of having an inflammatory disorder.

A subject is generally a mammal, for example a human, mouse, dog, cat, pig, horse, or non-human primate. In some embodiments, a subject is a human. In some embodiments, a subject in which a cell, tissue or organ is transduced is a vertebrate animal (e.g., a mammal or reptile). In some embodiments, a mammalian subject is a human, a non-human primate, a dog, a cat, a hamster, a mouse, a rat, a pig, a horse, a cow, a donkey or a rabbit. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, a subject is a model for a particular disease or used to study the pharmacokinetics and/or pharmacokinetics of a protein or siRNA encoded by a gene of interest.

A subject "having" a disease generally refers to a subject who exhibits one or more signs and/or symptoms of a particular disease. For example, a subject "having uveitis" may be a subject who exhibits one or more of the following signs and/or symptoms: burning of the eye, redness of the eye, blurred vision, photophobia, headache, dilated ciliary vessels, keratic precipitates, etc. In some embodiments, a subject "having" a disease has been diagnosed as having the disease by a medical professional (e.g., a medical doctor). In some embodiments, the diagnosis has been confirmed by a laboratory assay.

In some embodiments, a subject "suspected of having" a disease refers to a subject who is genetically predisposed (e.g., has one or more genetic factors, such as mutations) associated with increased risk of developing a particular disease. A subject "suspected of having" a disease may or may not exhibit one or more signs and/or symptoms of that disease. For example, a subject "suspected having an inflammatory disorder" may be a subject who does or does not exhibit one or more signs and/or symptoms of a disease but is characterized as having an increase in a marker of inflammation, such as Hemoglobin A1C, C-reactive protein (CRP), Serum ferratin, TNF-α, IFNγ, IL-1b, IL-6, an increase in T-cell activation, etc.

In some embodiments, a subject "having" a disease has been diagnosed as having the disease by a medical professional (e.g., a medical doctor). In some embodiments, the diagnosis has been confirmed by a laboratory assay. In some embodiments, a subject "suspected of having" a disease has been diagnosed as having the disease by a medical professional but the diagnosis has not been confirmed by a laboratory assay.

To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host cell, tissue or organ. A therapeutically acceptable amount may be an amount that is capable of treating a disease, e.g., an inflammatory disorder. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

In some embodiments, a specific tissue is targeted. For example, in some embodiments, a tissue or cell of the eye is targeted. In some embodiments, an rAAV is targeted to photoreceptor cells (e.g., rod cells, cone cells, retinal ganglion cells, etc.), bipolar cells, horizontal cells, epithelial cells, of the eye.

In some embodiments, a tissue or cell of the liver is targeted. Examples of liver cells include but are not limited to hepatocytes, parenchymal cells, non-parenchymal cells, sinusoidal endothelial cells, Kupffer cells, stellate cells, lymphocytes, etc.

In some embodiments, a tissue or cell of the heart is targeted. Examples of cardiac (heart) cells include but are not limited to cardiac muscle cells (e.g., cardiomyocytes), T-tubule cells, intercalated disc cells, fibroblasts, etc. In some embodiments, circulatory cells or tissue of a subject is targeted. Examples of circulatory cells and tissues include but are not limited to arteries, veins, capillaries, white blood cells, red blood cells, etc.

In some embodiments, a tissue or cell of the lung is targeted. Examples of lung tissue or cells include but are not limited to alveolar type I epithelial cells, alveolar type II cells, pneumocytes, capillary endothelial cells, macrophages, etc.

The disclosure relates, in some aspects, to methods for treating ischemia perfusion (e.g., as a result of an organ transplant) or transplantation rejection. In some embodiments, cells or tissue of a transplantation site of a subject are targeted. Generally, a transplantation site refers to a location on the body of a subject where an organ (or portion thereof) has been transplanted or tissue has been grafted. Examples of transplantation sites include but are not limited to a heart transplant site, a lung transplant site, a liver transplant site, a kidney transplant site, a skin graft site, etc.

EXAMPLES

Example 1: Serp-1 rAAV Constructs

Inflammation of the retina is a contributing factor in several of the leading causes of vision loss, such as diabetic retinopathy, age-related macular degeneration (AMD), and recurrent uveitis. SERP1 (also referred to herein as Serp-1) is a serine protease inhibitor isolated from the rabbit Myxoma virus. Generally, Serp-1 is secreted as a glycoprotein during late Myxoma virus infection. Serp-1 has been observed to inhibit multiple targets in the mammalian inflammatory cascade, giving it potent anti-inflammatory action. This example describes AAV-based delivery of serpins as anti-inflammatory gene therapies for ocular inflammatory diseases.

Figure 2:
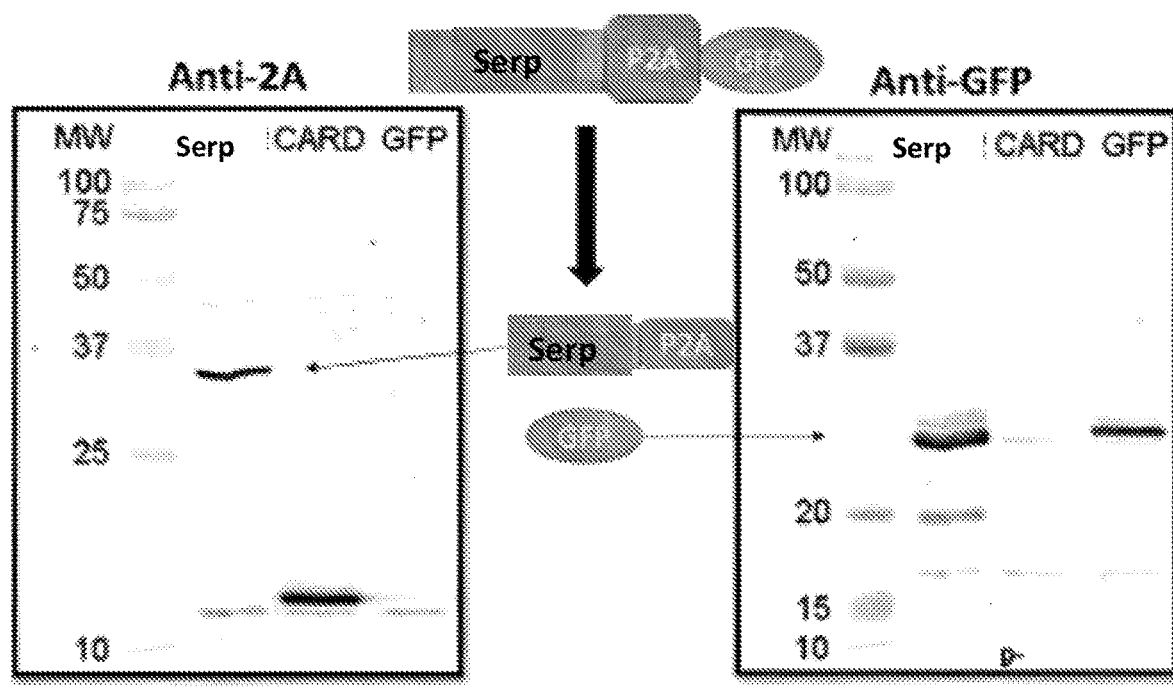
FIG. 2 shows a protein blot gel indicating Serp peptide expressed from an rAAV vector comprising a P2A self-cleaving peptide is separated from the GFP on translation. In this blot, anti-P2A antibody was used to detect the Serp peptide, which is fused to the P2A cleavage sequence.

A SERP1 transgene was fused to green fluorescent protein (GFP) with a self-cleaving porcine teschovirus-1 (P2A) peptide using the Gibson assembly method. These fused genes were cloned in plasmids containing AAV2 inverted terminal repeats (ITRs), and the resulting vector was referred to as SERP1-P2A-GFP. A schematic depicting a vector map of an AAV-Serp-1 vector is shown in FIG. 1. In vitro data indicate that upon expression, the P2A peptide self-cleaves to dissociate Serp-1 peptide from the GFP (FIG. 2).

Figure 3:
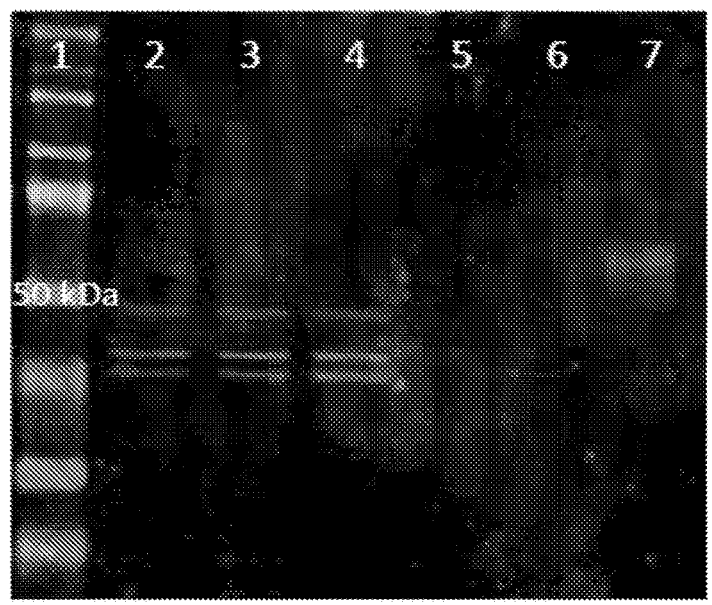
FIG. 3 shows a Western blot of Serp-1 transfected HEK293 cells. Well 1: ladder; Wells 2-4: lysate from HEK293T cells transfected with different clones, Well 5: empty, Well 6: conditioned media negative control, Well 7: SERP1 in conditioned media.
Figure 4:
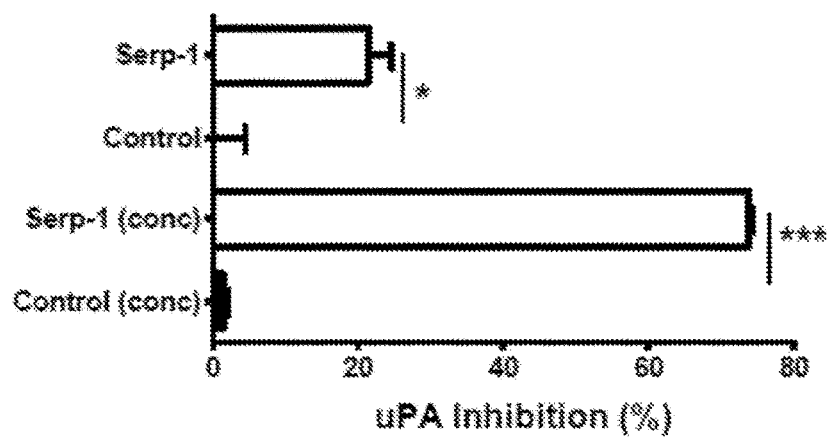
FIG. 4 shows data indicating that SERP1 conditioned media significantly inhibited urokinase plasminogen activator (uPA) activity in vitro.

HEK293T cells were transfected with SERP1-P2A-GFP using linear polyethyleneimine (PEI). Gene expression was measured by visualization of GFP via fluorescence microscopy after 48 hours. Western Blot confirmed the expression and cleavage of the secreted SERP1-P2A-GFP in the conditioned media (FIG. 3) and in the cell lysate. The inhibitory properties of Serp-1 peptide was measured using an in vitro assay for urokinase plasminogen activator activity (FIG. 4).

Figure 5:
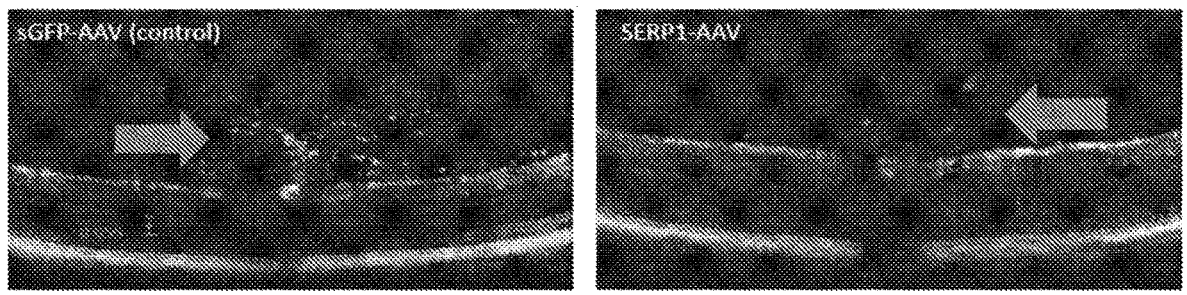
FIG. 5 shows Optical Coherence Tomography (OCT) indicating inflammatory cells (arrows) in the vitreous. Note the marked reduction of inflammatory cells in the SERP1-AAV treatment eye (right) compared to the sGFP-AAV control eye (left).
Figure 6:
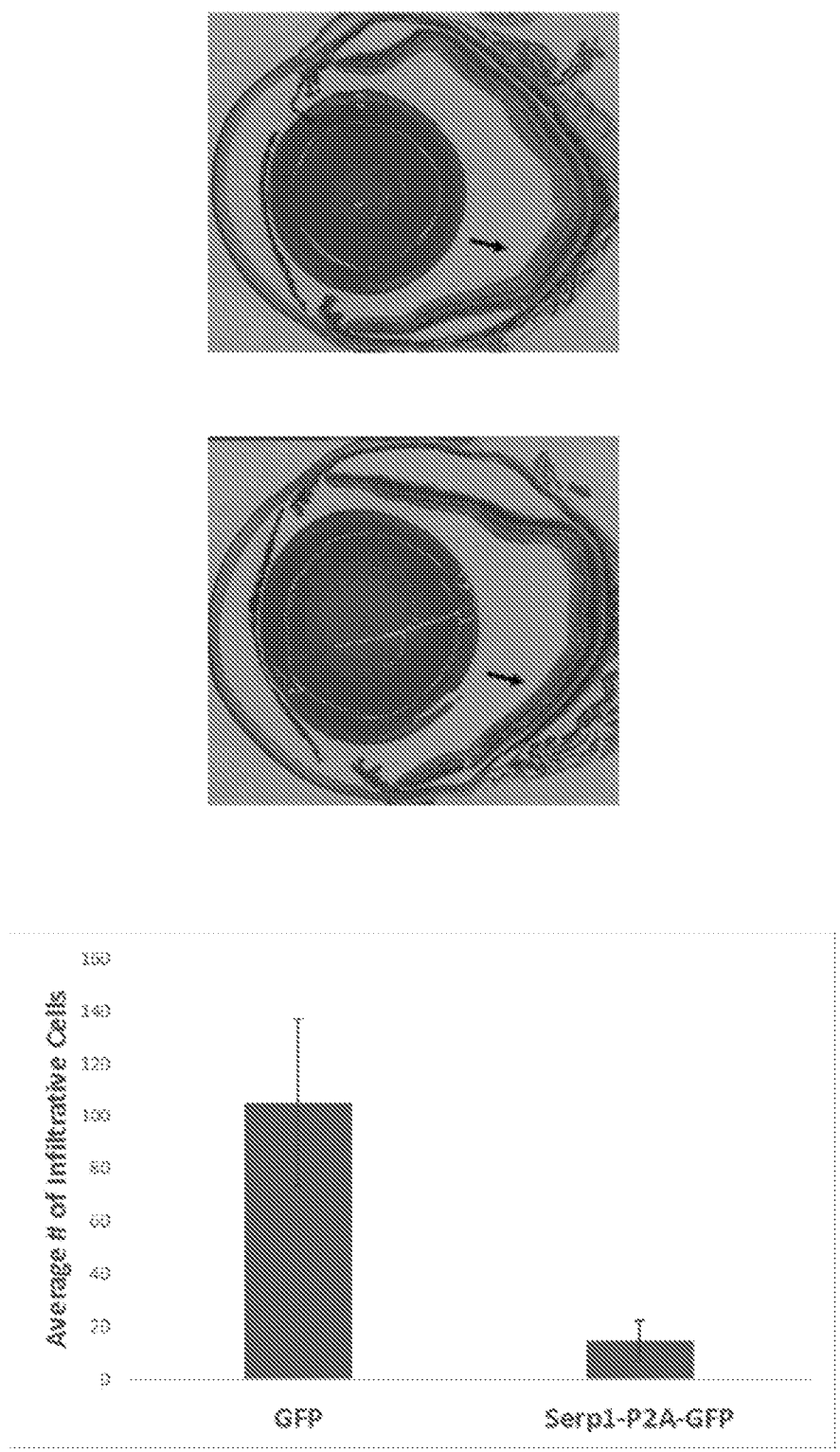
FIG. 6 shows hematoxylin and eosin (H&E) slides indicating fewer infiltrating leukocytes (arrows) in the vitreous of the SERP1-AAV treatment eye (bottom) compared to the sGFP-AAV control eye (top). The graph shows data indicating a significant reduction in inflammatory cell infiltration in the SERP1-AAV treatment eyes compared to GFP control eyes.

The SERP1 rAAV vector was packaged in AAV2 Quad+ T-V capsid protein, which have been observed to preferentially target the retina. An endotoxin-induced uveitis mouse model was used to test the efficacy of SERP1-AAV in vivo. C57BL/6 mice received an intravitreal injection of the SERP1-AAV therapy in one eye and sGFP-AAV in the other eye, acting as their own control. One month later, lipopolysaccharide (LPS) was injected into the vitreous of each eye to induce uveitis. The next day, a random sample of the mice was evaluated using Optical Coherence Tomography (OCT) in the vitreous (FIG. 5). Data indicate a marked reduction of inflammatory cells (arrows) in the SERP1-AAV treatment eye (right) compared to the sGFP-AAV control eye (left). All mice were then euthanized and the eyes were fixed, embedded, sectioned, and stained with H&E. The histopathology slides were used to enumerate the infiltrating leukocytes in the vitreous (FIG. 6). There was significantly less inflammation in the SERP1-AAV treatment eyes compared to the control eyes.

Example 2: rAAV-Serp-1 Therapeutic Methods

Diffuse alveolar hemorrhage (DAH) is an unusual complication of lupus with over 50% mortality. In both humans and mice, DAH is associated with ANCA-negative pulmonary capillaritis and hemosiderin-laden lung macrophages (Mϕ). C57BL/6 (B6) mice develop lupus complicated by severe DAH after intraperitoneal injection of pristane. It was observed that the pathogenesis of pristane-induced DAH requires Mφ and the uptake of dead cells opsonized by immunoglobulin and complement via complement receptor 3 (CR3, CD11b/CD18). In some embodiments, serpins (such as the rabbit Myxoma virus-derived Serp-1 protein) regulate coagulation and inflammation by binding serine proteases. Serp-1 has been observed to inhibit both thrombolytic (e.g., urokinase plasminogen activator) and thrombotic (e.g., Factor Xa) proteases and downregulates inflammation via its effects on Mφ function.

Pristane-treated B6 mice (21 per group) are intraperitoneally (i.p.) administered rAAV-Serp-1 or PBS from day 1 until d-14. In some experiments, Serp1 treatment is delayed until d-4 or Serp1 is given on days 1-3 only. The severity of DAH is evaluated by gross pathology and histology. Peritoneal cells and alveolar Mφ collected by bronchoalveolar lavage (BAL) are analyzed by flow cytometry.

Example 3: rAAV-Serp1 Injection of Mice

Figure 7:
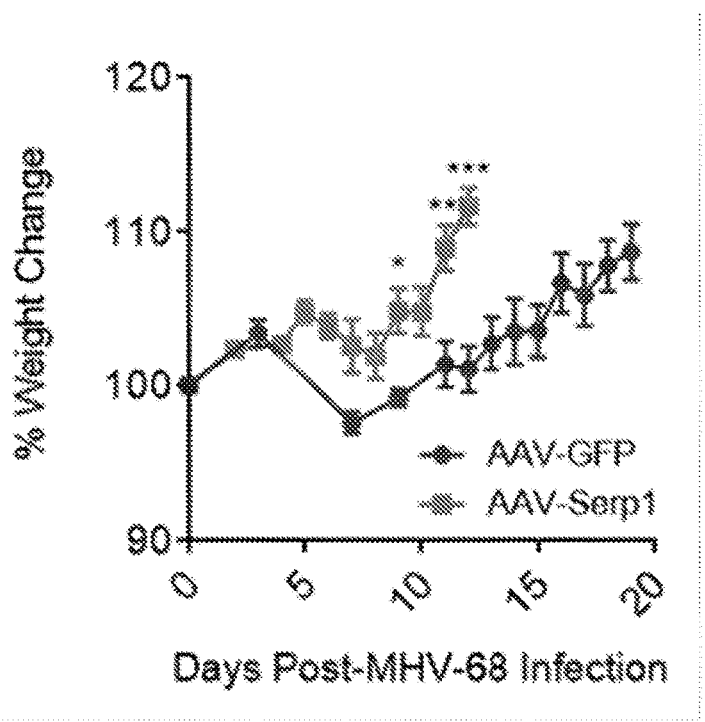
FIG. 7 shows data relating to percent weight change in MHV-68-infected mice after injection with AAV-Serp1 or AAVB-GFP.

AAV-sGFP-Serp1 was injected I.P. to IFNgR1-KO mice at the day of weaning (postnatal day 21) at a dose of $1\times10^{10}$ in 100 μL saline. 14 days later, infected mice were infected with 12.5×106 pfu MHV-68 (murine gammaherpes virus 68). Weight gain was measured as an indicator of health. Data indicates an improvement of weight change in AAV-Serp1-treated mice compared to AAV-GFP-injected mice (FIG. 7).

Example 4: Experimental Autoimmune Uveitis

Experimental autoimmune uveitis (EAU) is a mouse model of uveitis that mimics human uveitis. EAU is characterized by inflammation and vasculitis in the retina, choroid, photoreceptor destruction, and loss of vision. IL-2 is elevated leading to IFN-gamma-producing Th1 cells. IL-23 is elevated leading to IL-17-producing Th17 cells. IL-17 is a chemoattractant for neutrophils, macrophages, and monocytes and upregulates urokinase plasminogen activator (uPA), which is used by leukocytes to adhere to blood vessels and to infiltrate tissues. This example describes administration of Serp1-encoding rAAVs (e.g., AAV-Serp1) to EAU mice.

Figure 8:
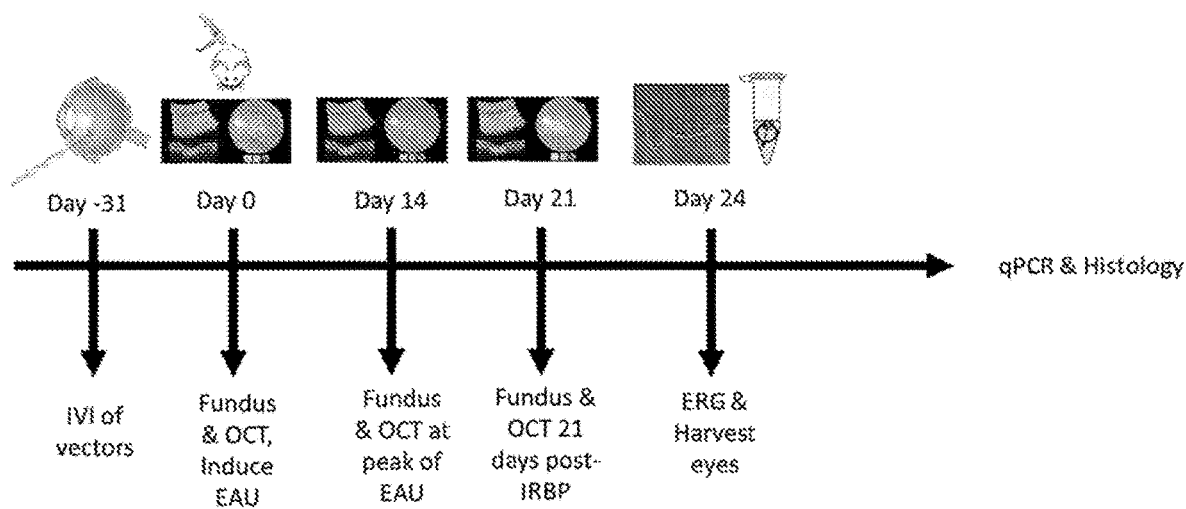
FIG. 8 shows experimental design for AAV-Serp1 treatment of an Experimental autoimmune uveitis (EAU) mouse model.

Injected B10.RIII mice intravitreally with $3\times10^{9}$ vg AAV-sGFP-Serp1 in one eye and an AAV-sGFP control vector in the other eye at 4 weeks old. Each mouse was its own control. Baseline fundus & OCT were performed one month later to confirm transgene expression and vector safety, then uveitis was induced with subcutaneous injections of Interphotoreceptor Binding Protein (IRBP) in Complete Freunds Adjuvant. Fundus images and optical coherence tomograms (OCT) were prepared at peak inflammation (14 days post-IRBP immunization). OCT and electroretinography (ERG) was performed again 21 days post immunization. A schematic of the experimental design is shown in FIG. 8.

Figure 9:
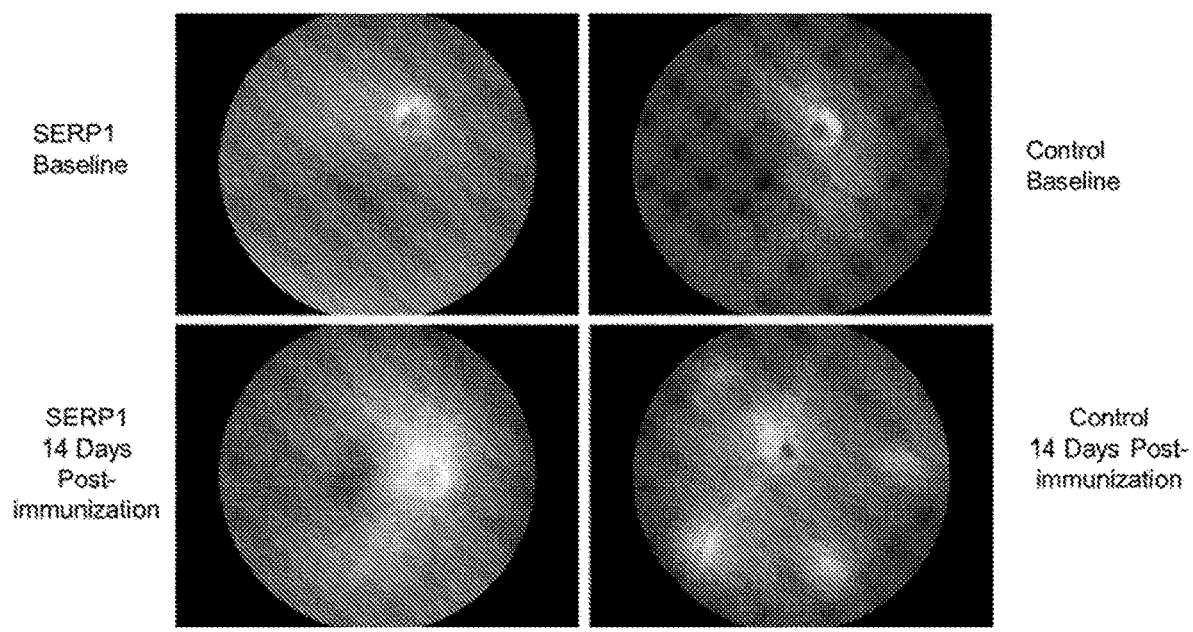
FIG. 9 shows data indicating reduced ocular inflammation following AAV-sGFP-Serp1 treatment in EAU mice.

Fundus images were taken at baseline and at 14 days post-immunization with IRBP, when peak inflammation is expected. As shown in FIG. 9, the blood vessels were dilated in both the treatment (AAV-Serp1) and control eyes, but the control (AAV-sGFP) eyes showed more signs of inflammation, including perivascular lesions (arrow) and blurring of the optic disk (arrowhead) indicative of edema.

Figure 10:
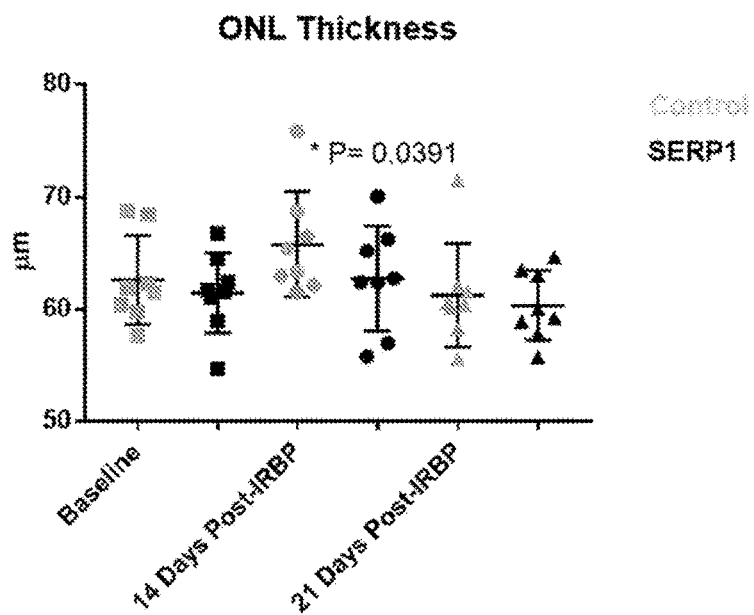
FIG. 10 shows data indicating a reduction of retinal edema in EAU mice following treatment with AAV-sGFP-Serp1.

FIG. 10 shows reduction of retinal edema following treatment with AAV-sGFP-Serp1. Thickness of the outer nuclear layer of the retina was measured by optical coherence tomography (OCT). More thickening, indicative of edema, was seen in the control eyes vs SERP1 eyes at peak inflammation (FIG. 10).

Figure 11:
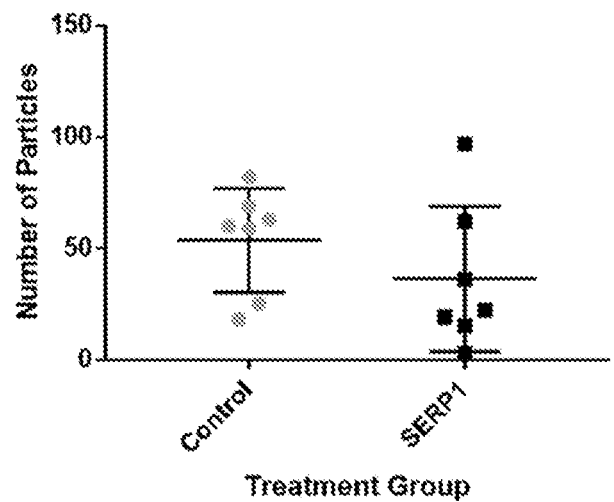
FIG. 11 shows data indicating a reduction in infiltrating cells in eyes of EAU mice following treatment with AAV-sGFP-Serp1
Figure 11:
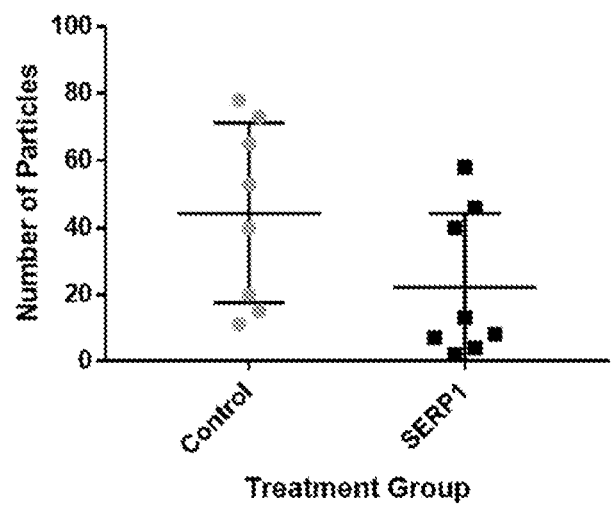
Figure 12:
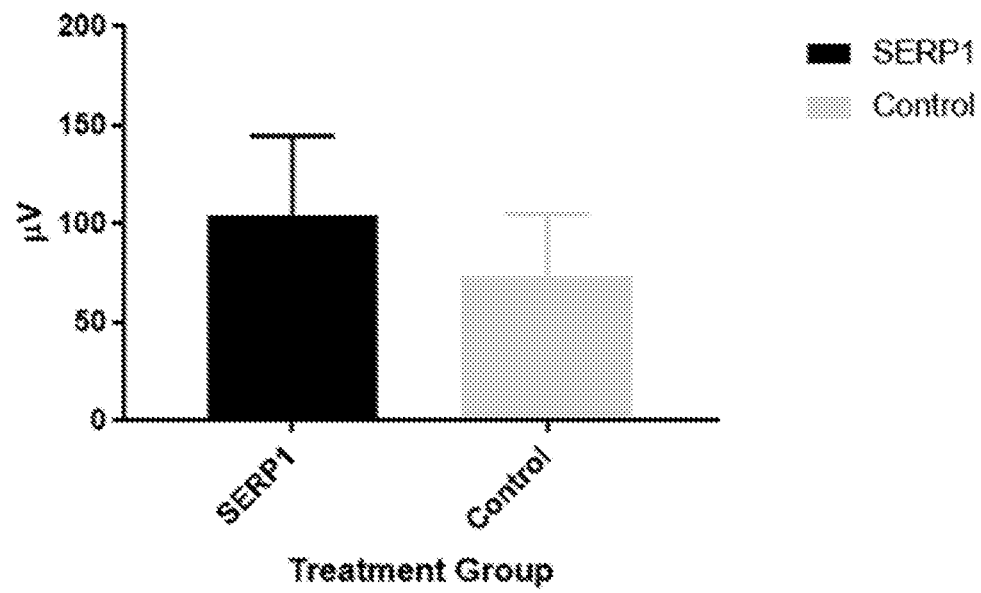
FIG. 12 shows data indicating improved retinal function in AAV-Serp1-treated mice relative to control mice. Top panel shows ERG "a-wave" amplitudes of photoreceptor cells. Bottom panel shows "b-wave" amplitudes of bipolar cells.
Figure 12:
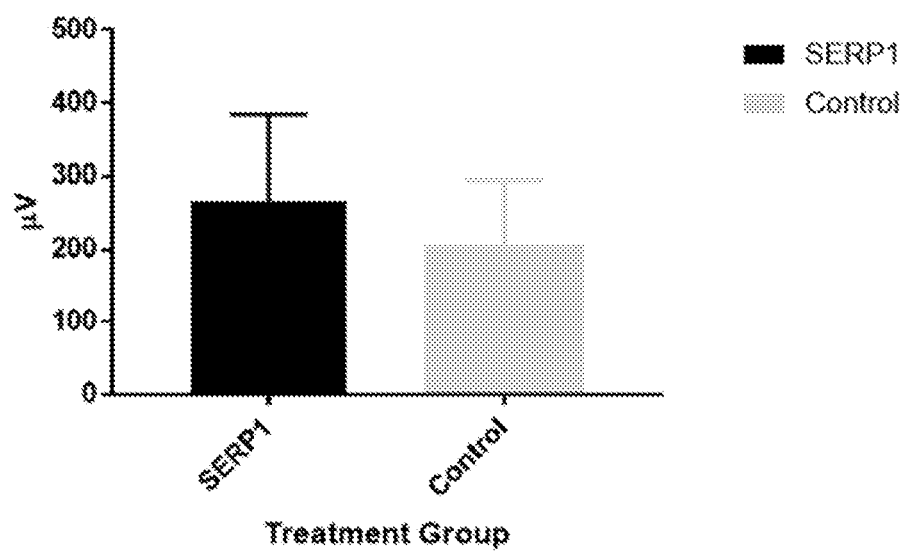

As described above, data indicates that Serp1 conditioned medium inhibits uPA and blocks cellular infiltrates in a model of infectious uveitis induced by injection of bacterial endotoxin. In the mouse EAU model, administration of AAV-Serp1 resulted in a reduction of infiltrating cells (FIG. 11). More particles, indicative of leukocyte infiltration, were observed in the control eyes compared to AAV-SERP1-treated eyes at peak inflammation and at 21 days post-IRBP. Improved retinal function was also observed in AAV-Serp1-treated mice (FIG. 12). Retinal function was measured by comparing ERG of treated eyes relative to control eyes.

What is claimed is:

1. A recombinant adeno-associated virus (rAAV) vector comprising an isolated nucleic acid encoding a serine proteinase inhibitor 1 (Serp-1) peptide, flanked by two adeno-associated virus (AAV) inverted terminal repeat (ITR) sequences, wherein the rAAV vector comprises the nucleic acid sequence set forth in any one of SEQ ID NOs: 2-4.

2. The rAAV vector of claim 1, wherein the Serp-1 peptide comprises an amino acid sequence that is at least 90% identical to the amino acid sequence set forth in SEQ ID NO: 1.

3. The rAAV vector of claim 1, wherein the Serp-1 peptide consists of the amino acid sequence set forth in SEQ ID NO: 1.

4. A recombinant adeno-associated virus (rAAV) particle comprising:
   (i) the rAAV vector of claim 1; and
   (ii) one or more adeno-associated virus (AAV) capsid proteins.

5. The rAAV of claim 4, wherein the one or more AAV capsid proteins is of a serotype selected from serotype 2, 3, 4, 5, 6, 7, 8, 9, 10.

6. The rAAV of claim 4, wherein the one or more AAV capsid proteins is of an AAV2 serotype variant.

7. The rAAV of claim 6, wherein the AAV2 serotype variant comprises one or more mutation selected from Y272F, Y444F, Y500F, Y730F, and T491V.

8. The rAAV of claim 7, wherein the AAV2 serotype is an AAV2 Quad+T-V variant.

9. The rAAV of claim 4, wherein the one or more AAV capsid proteins is of an AAV6 serotype variant.

10. The rAAV of claim 9, wherein the AAV6 serotype variant comprises one or more mutations selected from Y705F, Y731F, and T492V.

11. The rAAV of claim 10, wherein the AAV6 serotype variant comprises Y705F, Y731F, and T492V mutations.

12. An isolated cell comprising the rAAV of claim 4.

13. The isolated cell of claim 12, wherein the isolated cell is a bacterial cell, a mammalian cell, or an insect cell.

14. The isolated cell of claim 13, wherein the mammalian cell is a HEK293 cell.

15. The isolated cell of claim 13, wherein the insect cell is an Sf9 cell.

* * * * *

SEQUENCE LISTING

```
<160> NUMBER OF SEQ ID NOS: 7

<210> SEQ ID NO 1
<211> LENGTH: 369
<212> TYPE: PRT
<213> ORGANISM: Artificial Sequence
<220> FEATURE:
<223> OTHER INFORMATION: Synthetic Polypeptide

<400> SEQUENCE: 1

Met Lys Tyr Leu Val Leu Val Leu Cys Leu Thr Ser Cys Ala Cys Arg
1               5                   10                  15

Asp Ile Gly Leu Trp Thr Phe Arg Tyr Val Tyr Asn Glu Ser Asp Asn
            20                  25                  30

Val Val Phe Ser Pro Tyr Gly Leu Thr Ser Ala Leu Ser Val Leu Arg
        35                  40                  45

Ile Ala Ala Gly Gly Asn Thr Lys Arg Glu Ile Asp Val Pro Glu Ser
    50                  55                  60

Val Val Glu Asp Ser Asp Ala Phe Leu Ala Leu Arg Glu Leu Phe Val
65                  70                  75                  80

Asp Ala Ser Val Pro Leu Arg Pro Glu Phe Thr Ala Glu Phe Ser Ser
                85                  90                  95
```

```
Arg Phe Asn Thr Ser Val Gln Arg Val Thr Phe Asn Ser Glu Asn Val
                100                 105                 110
Lys Asp Val Ile Asn Ser Tyr Val Lys Asp Lys Thr Gly Gly Asp Val
            115                 120                 125
Pro Arg Val Leu Asp Ala Ser Leu Asp Arg Asp Thr Lys Met Leu Leu
        130                 135                 140
Leu Ser Ser Val Arg Met Lys Thr Ser Trp Arg His Val Phe Asp Pro
145                 150                 155                 160
Ser Phe Thr Thr Asp Gln Pro Phe Tyr Ser Gly Asn Val Thr Tyr Lys
                165                 170                 175
Val Arg Met Met Asn Lys Ile Asp Thr Leu Lys Thr Glu Thr Phe Thr
            180                 185                 190
Leu Arg Asn Val Gly Tyr Ser Val Thr Glu Leu Pro Tyr Lys Arg Arg
        195                 200                 205
Gln Thr Ala Met Leu Leu Val Val Pro Asp Asp Leu Gly Glu Ile Val
    210                 215                 220
Arg Ala Leu Asp Leu Ser Leu Val Arg Phe Trp Ile Arg Asn Met Arg
225                 230                 235                 240
Lys Asp Val Cys Gln Val Val Met Pro Lys Phe Ser Val Glu Ser Val
                245                 250                 255
Leu Asp Leu Arg Asp Ala Leu Gln Arg Leu Gly Val Arg Asp Ala Phe
            260                 265                 270
Asp Pro Ser Arg Ala Asp Phe Gly Gln Ala Ser Pro Ser Asn Asp Leu
        275                 280                 285
Tyr Val Thr Lys Val Leu Gln Thr Ser Lys Ile Glu Ala Asp Glu Arg
    290                 295                 300
Gly Thr Thr Ala Ser Ser Asp Thr Ala Ile Thr Leu Ile Pro Arg Asn
305                 310                 315                 320
Ala Leu Thr Ala Ile Val Ala Asn Lys Pro Phe Met Phe Leu Ile Tyr
                325                 330                 335
His Lys Pro Thr Thr Thr Val Leu Phe Met Gly Thr Ile Thr Lys Gly
            340                 345                 350
Glu Lys Val Ile Tyr Asp Thr Glu Gly Arg Asp Val Val Ser Ser
        355                 360                 365
Val

<210> SEQ ID NO 2
<211> LENGTH: 6290
<212> TYPE: DNA
<213> ORGANISM: Artificial Sequence
<220> FEATURE:
<223> OTHER INFORMATION: Synthetic Polynucleotide

<400> SEQUENCE: 2 agggggggggg gggggggggt tggccactcc ctctctgcgc gctcgctcgc tcactgaggc    60
cgggcgacca aggtcgccc gacgcccggg ctttgcccgg gcggcctcag tgagcgagcg    120
agcgcgcaga gagggagtgg ccaactccat cactaggggt tcctcagatc tgaattcggt    180
accctagtta ttaatagtaa tcaattacgg ggtcattagt tcatagccca tatatggagt    240
tccgcgttac ataacttacg gtaaatggcc cgcctggctg accgcccaac gacccccgcc    300
cattgacgtc aataatgacg tatgttccca tagtaacgcc aatagggact ttccattgac    360
gtcaatgggt ggactattta cggtaaactg cccacttggc agtacatcaa gtgtatcata    420
tgccaagtac gccccctatt gacgtcaatg acggtaaatg gcccgcctgg cattatgccc    480
```

```
agtacatgac cttatgggac tttcctactt ggcagtacat ctacgtatta gtcatcgcta    540
ttaccatggt cgaggtgagc cccacgttct gcttcactct ccccatctcc cccccctccc    600
cacccccaat tttgtattta tttatttttt aattattttg tgcagcgatg ggggcggggg    660
gggggggggg gcgcgcgcca ggcggggcgg ggcggggcga ggggcggggc ggggcgaggc    720
ggagaggtgc ggcggcagcc aatcagagcg gcgcgctccg aaagtttcct tttatggcga    780
ggcggcggcg gcgcggcccc tataaaaagc gaagcgcgcg gcgggcggga gtcgctgcga    840
cgctgccttc gccccgtgcc ccgctccgcc gccgcctcgc gccgcccgcc ccggctctga    900
ctgaccgcgt tactcccaca ggtgagcggg cgggacggcc cttctcctcc gggctgtaat    960
tagcgcttgg tttaatgacg gcttgtttct tttctgtggc tgcgtgaaag ccttgagggg   1020
ctccgggagc tagagcctct gctaaccatg ttcatgcctt cttcttttc ctacagctcc    1080 tgggcaacgt gctggttatt gtgctgtctc atcattttgg caaagaattc ctcgaagaac   1140
taggcaacgc gtctcgaggc caccatgaag tatctggtcc tcgtcttatg tttaacgtcg   1200
tgcgcgtgtc gagatatcgg actatggacg ttccgatacg tctacaacga aagcgacaac   1260
gtcgtgttct caccgtacgg cttgacctcc gcgttgtccg tgttacggat cgcggcgggc   1320
ggtaacacga aacgagaaat agacgtcccc gaatccgtcg tggaggactc cgacgccttt   1380
ctcgcgttac gggagttgtt cgtagacgca tccgttccgt tacgtcccga gtttacggcg   1440
gagttctcct cgcgattcaa tacctccgtg caacgcgtga cgtttaactc ggagaacgtc   1500
aaagacgtca ttaactcgta cgttaaggat aagacgggag gagacgtccc acgcgtattg   1560
gacgcctccc tagaccgaga tactaaaatg ctgctattga gctccgttcg tatgaagacg   1620
agctggagac acgtattcga cccttcgttc acgacggatc aacctttta ttccggaaac    1680 gtcacataca aggtacgtat gatgaataaa atagatacgt gaaaacgga dacgtttacg    1740 cttagaaacg tgggatactc cgtaacgaaa ctgccgtata acggcgtca aacgccatg     1800 ttgctcgtcg ttccggacga cttgggagag atcgtgcggg ccctcgatct ttctctagta   1860
cgcttctgga tacgcaacat gaggaaagac gtgtgtcagg tggtaatgcc caagttctcc   1920
gtcgaatcgg tcctggatct gagggacgcc ctccagagac tgggggtgcg agacgcgttc   1980
gatccatccc gggcggactt cggtcaggcg tccccgtcga acgatctata cgtcacgaag   2040
gtgttacaga cgtccaagat agaggcggac gaacggggaa cgacggcgtc gagcgacaca   2100
gccatcaccc tcatcccag gaacgccctc acggcgatcg tggcgaacaa accgtttatg    2160
tttctcatct atcacaagcc tacaacgacc gtgttgttta tgggaacgat aacaaagggt   2220
gaaaaagtaa tatacgatac ggagggtcga gatgatgtcg tatcctctgt agcggccgct   2280
gctactaact tcagcctgct gaagcaggct ggagacgtgg aggagaaccc tggaccttcc   2340
ggaatgagca agggcgagga actgttcact ggcgtggtcc caattctcgt ggaactggat   2400
ggcgatgtga atgggcacaa attttctgtc agcggagagg gtgaaggtga tgccacatac   2460
ggaaagctca ccctgaaatt catctgcacc actggaaagc tccctgtgcc atggccaaca   2520
ctggtcacta ccctgaccta tggcgtgcag tgcttttcca gatacccaga ccatatgaag   2580
cagcatgact ttttcaagag cgccatgccc gagggctatg tgcaggagag aaccatcttt   2640
ttcaaagatg acgggaacta caagacccgc gctgaagtca agttcgaagg tgacaccctg   2700
gtgaatagaa tcgagctgaa gggcattgac tttaaggagg atggaaacat tctcggccac   2760
aagctggaat acaactataa ctcccacaat gtgtacatca tggccgacaa gcaaaagaat   2820
```

```
ggcatcaagg tcaacttcaa gatcagacac aacattgagg atggatccgt gcagctggcc      2880
gaccattatc aacagaacac tccaatcggc gacggccctg tgctcctccc agacaaccat      2940
tacctgtcca cccagtctgc cctgtctaaa gatcccaacg aaaagagaga ccacatggtc      3000
ctgctggagt tgtgaccgc tgctgggatc acacatggca tggacgagct gtacaagtga       3060
atgcatgcgg ccgcgcggat ccagacatga taagatacat tgatgagttt ggacaaacca     3120
caactagaat gcagtgaaaa aaatgcttta tttgtgaaat ttgtgatgct attgctttat      3180
ttgtaaccat tataagctgc aataaacaag ttaacaacaa caattgcatt cattttatgt      3240
ttcaggttca gggggaggtg tgggaggttt tttagtcgac tggggagaga tctgaggaac      3300
ccctagtgat ggagttggcc actccctctc tgcgcgctcg ctcgctcact gaggccgccc      3360
gggcaaagcc cgggcgtcgg gcgacctttg gtcgcccggc ctcagtgagc gagcgagcgc      3420
gcagagaggg agtggccaac cccccccccc ccccccctgc agccctgcat taatgaatcg      3480
gccaacgcgc ggggagaggc ggtttgcgta ttgggcgctc ttccgcttcc tcgctcactg      3540
actcgctgcg ctcggtcgtt cggctgcggc gagcggtatc agctcactca aaggcggtaa      3600
tacggttatc cacagaatca ggggataacg caggaaagaa catgtgagca aaaggccagc      3660
aaaaggccag gaaccgtaaa aaggccgcgt tgctggcgtt tttccatagg ctccgccccc      3720
ctgacgagca tcacaaaaat cgacgctcaa gtcagaggtg gcgaaacccg acaggactat      3780
aaagatacca ggcgtttccc cctggaagct ccctcgtgcg ctctcctgtt ccgaccctgc      3840
cgcttaccgg atacctgtcc gcctttctcc cttcgggaag cgtggcgctt tctcaatgct      3900
cacgctgtag gtatctcagt tcggtgtagg tcgttcgctc caagctgggc tgtgtgcacg      3960
aaccccccgt tcagcccgac cgctgcgcct tatccggtaa ctatcgtctt gagtccaacc      4020
cggtaagaca cgacttatcg ccactggcag cagccactgg taacaggatt agcagagcga      4080
ggtatgtagg cggtgctaca gagttcttga agtggtggcc taactacggc tacactagaa      4140
ggacagtatt tggtatctgc gctctgctga agccagttac cttcggaaaa agagttggta      4200
gctcttgatc cggcaaacaa accaccgctg gtagcggtgg ttttttgtt tgcaagcagc      4260 agattacgcg cagaaaaaaa ggatctcaag aagatccttt gatcttttct acggggtctg      4320
acgctcagtg gaacgaaaac tcacgttaag ggattttggt catgagatta tcaaaaagga      4380
tcttcaccta gatcctttta aattaaaaat gaagttttaa atcaatctaa agtatatatg      4440
agtaaacttg gtctgacagt taccaatgct taatcagtga ggcacctatc tcagcgatct      4500
gtctatttcg ttcatccata gttgcctgac tccccgtcgt gtagataact acgatacggg      4560
agggcttacc atctggcccc agtgctgcaa tgataccgcg agacccacgc tcaccggctc      4620
cagatttatc agcaataaac cagccagccg gaagggccga gcgcagaagt ggtcctgcaa      4680
ctttatccgc ctccatccag tctattaatt gttgccggga agctagagta agtagttcgc      4740
cagttaatag tttgcgcaac gttgttgcca ttgctacagg catcgtggtg tcacgctcgt      4800
cgtttggtat ggcttcattc agctccggtt cccaacgatc aaggcgagtt acatgatccc      4860
ccatgttgtg caaaaaagcg gttagctcct tcggtcctcc gatcgttgtc agaagtaagt      4920
tggccgcagt gttatcactc atggttatgg cagcactgca taattctctt actgtcatgc      4980
catccgtaag atgcttttct gtgactggtg agtactcaac caagtcattc tgagaatagt      5040
gtatgcggcg accgagttgc tcttgcccgg cgtcaatacg ggataatacc gcgccacata      5100
gcagaacttt aaaagtgctc atcattggaa aacgttcttc ggggcgaaaa ctctcaagga      5160
tcttaccgct gttgagatcc agttcgatgt aacccactcg tgcacccaac tgatcttcag      5220
```

-continued

| | |
|---|---|
| catcttttac tttcaccagc gtttctgggt gagcaaaaac aggaaggcaa aatgccgcaa | 5280 |
| aaaagggaat aagggcgaca cggaaatgtt gaatactcat actcttcctt tttcaatatt | 5340 |
| attgaagcat ttatcagggt tattgtctca tgagcggata catatttgaa tgtatttaga | 5400 |
| aaaataaaca aataggggtt ccgcgcacat ttccccgaaa agtgccacct gacgtctaag | 5460 |
| aaaccattat tatcatgaca ttaacctata aaaataggcg tatcacgagg ccctttcgtc | 5520 |
| tcgcgcgttt cggtgatgac ggtgaaaacc tctgacacat gcagctcccg gagacggtca | 5580 |
| cagcttgtct gtaagcggat gccgggagca gacaagcccg tcagggcgcg tcagcgggtg | 5640 |
| ttggcgggtg tcggggctgg cttaactatg cggcatcaga gcagattgta ctgagagtgc | 5700 |
| accatatgcg gtgtgaaata ccgcacagat gcgtaaggag aaaataccgc atcaggaaat | 5760 |
| tgtaaacgtt aatattttgt taaaattcgc gttaaatttt tgttaaatca gctcattttt | 5820 |
| taaccaatag gccgaaatcg gcaaaatccc ttataaatca aaagaataga ccgagatagg | 5880 |
| gttgagtgtt gttccagttt ggaacaagag tccactatta agaacgtgg actccaacgt | 5940 |
| caaagggcga aaaccgtct atcagggcga tggcccacta cgtgaaccat caccctaatc | 6000 |
| aagttttttg gggtcgaggt gccgtaaagc actaaatcgg aacctaaag ggagcccccg | 6060 |
| atttagagct tgacggggaa agccggcgaa cgtggcgaga aggaaggga agaaagcgaa | 6120 |
| aggagcgggc gctagggcgc tggcaagtgt agcggtcacg ctgcgcgtaa ccaccacacc | 6180 |
| cgccgcgctt aatgcgccgc tacagggcgc gtcgcgccat tcgccattca ggctacgcaa | 6240 |
| ctgttgggaa gggcgatcgg tgcgggcctc ttcgctatta cgccaggctg | 6290 |

<210> SEQ ID NO 3
<211> LENGTH: 5514
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| agggggggg gggggggggt tggccactcc ctctctgcgc gctcgctcgc tcactgaggc | 60 |
| cgggcgacca aaggtcgccc gacgcccggg ctttgcccgg gcggcctcag tgagcgagcg | 120 |
| agcgcgcaga gagggagtgg ccaactccat cactagggt tcctcagatc tgaattcggt | 180 |
| accctagtta ttaatagtaa tcaattacgg ggtcattagt tcatagccca tatatggagt | 240 |
| tccgcgttac ataacttacg gtaaatggcc cgcctggctg accgcccaac gacccccgcc | 300 |
| cattgacgtc aataatgacg tatgttccca tagtaacgcc aatagggact ttccattgac | 360 |
| gtcaatgggt ggactattta cggtaaactg cccacttggc agtacatcaa gtgtatcata | 420 |
| tgccaagtac gccccctatt gacgtcaatg acggtaaatg gcccgcctgg cattatgccc | 480 |
| agtacatgac cttatgggac tttcctactt ggcagtacat ctacgtatta gtcatcgcta | 540 |
| ttaccatggt cgaggtgagc ccacgttct gcttcactct cccatctcc cccccctccc | 600 |
| cacccccaat tttgtattta ttattttt aattattttg tgcagcgatg ggggcggggg | 660 |
| gggggggggg gcgcgcgcca ggcggggcgg ggcggggcga ggggcggggc ggggcgaggc | 720 |
| ggagaggtgc ggcggcagcc aatcagagcg gcgcgctccg aaagtttcct tttatggcga | 780 |
| ggcggcggcg gcggcggccc tataaaaagc gaagcgcgcg gcgggcggga gtcgctgcga | 840 |
| cgctgccttc gccccgtgcc ccgctccgcc gccgcctcgc gccgcccgcc ccggctctga | 900 |
| ctgaccgcgt tactcccaca ggtgagcggg cgggacggcc cttctcctcc gggctgtaat | 960 |

-continued

```
tagcgcttgg tttaatgacg gcttgtttct tttctgtggc tgcgtgaaag ccttgagggg    1020
ctccgggagc tagagcctct gctaaccatg ttcatgcctt cttcttttc ctacagctcc     1080 tgggcaacgt gctggttatt gtgctgtctc atcattttgg caaagaattc ctcgaagaac    1140
taggcaacgt gtctcgaggc caccatgaag tatctggtcc tcgtcttatg tttaacgtcg    1200
tgcgcgtgtc gagatatcgg actatggacg ttccgatacg tctacaacga aagcgacaac    1260
gtcgtgttct caccgtacgg cttgacctcc gcgttgtccg tgttacggat cgcggcgggc    1320
ggtaacacga aacgagaaat agacgtcccc gaatccgtcg tggaggactc cgacgccttt    1380
ctcgcgttac gggagttgtt cgtagacgca tccgttccgt tacgtcccga gtttacggcg    1440
gagttctcct cgcgattcaa tacctccgtg caacgcgtga cgtttaactc ggagaacgtc    1500
aaagacgtca ttaactcgta cgttaaggat aagacgggag gagacgtccc acgcgtattg    1560
gacgcctccc tagaccgaga tactaaaatg ctgctattga gctccgttcg tatgaagacg    1620
agctggagac acgtattcga cccttcgttc acgacggatc aacctttta ttccggaaac     1680 gtcacataca aggtacgtat gatgaataaa atagatacgt tgaaaacgga gacgtttacg    1740
cttagaaacg tgggatactc cgtaacggaa ctgccgtata aacggcgtca aacggccatg    1800
ttgctcgtcg ttccggacga cttggggaga tcgtgcggg ccctcgatct ttctctagta     1860
cgcttctgga tacgcaacat gaggaaagac gtgtgtcagg tggtaatgcc caagttctcc    1920
gtcgaatcgg tcctggatct gagggacgcc ctccagagac tggggtgcg agacgcgttc     1980 gatccatccc gggcggactt cggtcaggcg tccccgtcga acgatctata cgtcacgaag    2040
gtgttacaga cgtccaagat agaggcggac gaacggggaa cgacggcgtc gagcgacaca    2100
gccatcaccc tcatccccag gaacgccctc acggcgatcg tggcgaacaa accgtttatg    2160
tttctcatct atcacaagcc tacaacgacc gtgttgttta tgggaacgat aacaaagggt    2220 gaaaagtaa tatacgatac ggagggtcga gatgatgtcg tatcctctgt agcggccgct     2280
tgaatgcatg cggccgcgcg gatccagaca tgataagata cattgatgag tttgacaaa     2340 ccacaactag aatgcagtga aaaaaatgct ttatttgtga aatttgtgat gctattgctt    2400
tatttgtaac cattataagc tgcaataaac aagttaacaa caacaattgc attcatttta    2460
tgtttcaggt tcagggggag gtgtgggagg ttttttagtc gactggggag agatctgagg    2520 aaccctagt gatggagttg gccactccct ctctgcgcgc tcgctcgctc actgaggccg     2580
cccgggcaaa gcccgggcgt cgggcgacct ttggtcgccc ggcctcagtg agcgagcgag    2640
cgcgcagaga gggagtggcc aacccccccc cccccccccc tgcagccctg cattaatgaa    2700
tcggccaacg cgcggggaga ggcggtttgc gtattgggcg ctcttccgct tcctcgctca    2760
ctgactcgct gcgctcggtc gttcggctgc ggcgagcggt atcagctcac tcaaaggcgg    2820
taatacggtt atccacagaa tcaggggata acgcaggaaa gaacatgtga gcaaaaggcc    2880
agcaaaaggc caggaaccgt aaaaaggccg cgttgctggc gttttccat aggctccgcc     2940 cccctgacga gcatcacaaa aatcgacgct caagtcagag gtggcgaaac ccgacaggac    3000
tataaagata ccaggcgttt cccctggaa gctccctcgt gcgctctcct gttccgaccc     3060
tgccgcttac cggatacctg tccgccttc tcccttcggg aagcgtggcg ctttctcaat     3120
gctcacgctg taggtatctc agttcggtgt aggtcgttcg ctccaagctg gctgtgtgc     3180 acgaaccccc cgttcagccc gaccgctgcg ccttatccgg taactatcgt cttgagtcca    3240
acccggtaag acacgactta tcgccactgg cagcagccac tggtaacagg attagcagag    3300
cgaggtatgt aggcggtgct acagagttct tgaagtggtg gcctaactac ggctacacta    3360
```

```
gaaggacagt atttggtatc tgcgctctgc tgaagccagt taccttcgga aaaagagttg    3420
gtagctcttg atccggcaaa caaaccaccg ctggtagcgg tggttttttt gtttgcaagc    3480
agcagattac gcgcagaaaa aaaggatctc aagaagatcc tttgatcttt tctacggggt    3540
ctgacgctca gtggaacgaa aactcacgtt aagggatttt ggtcatgaga ttatcaaaaa    3600
ggatcttcac ctagatcctt ttaaattaaa aatgaagttt taaatcaatc taaagtatat    3660
atgagtaaac ttggtctgac agttaccaat gcttaatcag tgaggcacct atctcagcga    3720
tctgtctatt tcgttcatcc atagttgcct gactccccgt cgtgtagata actacgatac    3780
gggagggctt accatctggc cccagtgctg caatgatacc gcgagaccca cgctcaccgg    3840
ctccagattt atcagcaata aaccagccag ccggaagggc cgagcgcaga agtggtcctg    3900
caactttatc cgcctccatc cagtctatta attgttgccg ggaagctaga gtaagtagtt    3960
cgccagttaa tagtttgcgc aacgttgttg ccattgctac aggcatcgtg gtgtcacgct    4020
cgtcgtttgg tatggcttca ttcagctccg gttcccaacg atcaaggcga gttacatgat    4080
cccccatgtt gtgcaaaaaa gcggttagct ccttcggtcc tccgatcgtt gtcagaagta    4140
agttggccgc agtgttatca ctcatggtta tggcagcact gcataattct cttactgtca    4200
tgccatccgt aagatgcttt tctgtgactg gtgagtactc aaccaagtca ttctgagaat    4260
agtgtatgcg gcgaccgagt tgctcttgcc cggcgtcaat acgggataat accgcgccac    4320
atagcagaac tttaaaagtg ctcatcattg gaaaacgttc ttcggggcga aaactctcaa    4380
ggatcttacc gctgttgaga tccagttcga tgtaacccac tcgtgcaccc aactgatctt    4440
cagcatcttt tactttcacc agcgtttctg ggtgagcaaa aacaggaagg caaaatgccg    4500
caaaaaaggg aataagggcg acacggaaat gttgaatact catactcttc ctttttcaat    4560
attattgaag catttatcag ggttattgtc tcatgagcgg atacatattt gaatgtattt    4620
agaaaaataa acaaataggg gttccgcgca catttccccg aaaagtgcca cctgacgtct    4680
aagaaaccat tattatcatg acattaacct ataaaaatag gcgtatcacg aggccctttc    4740
gtctcgcgcg tttcggtgat gacggtgaaa acctctgaca catgcagctc ccggagacgg    4800
tcacagcttg tctgtaagcg gatgccggga gcagacaagc ccgtcagggc gcgtcagcgg    4860
gtgttggcgg gtgtcggggc tggcttaact atgcggcatc agagcagatt gtactgagag    4920
tgcaccatat gcggtgtgaa ataccgcaca gatgcgtaag gagaaaatac cgcatcagga    4980
aattgtaaac gttaatattt tgttaaaatt cgcgttaaat ttttgttaaa tcagctcatt    5040
ttttaaccaa taggccgaaa tcggcaaaat cccttataaa tcaaaagaat agaccgagat    5100
agggttgagt gttgttccag tttggaacaa gagtccacta ttaaagaacg tggactccaa    5160
cgtcaaaggg cgaaaaaccg tctatcaggg cgatggccca ctacgtgaac catcacccta    5220
atcaagtttt ttggggtcga ggtgccgtaa agcactaaat cggaaccota aagggagccc    5280
ccgatttaga gcttgacggg gaaagccggc gaacgtggcg agaaaggaag ggaagaaagc    5340
gaaaggagcg ggcgctaggg cgctggcaag tgtagcggtc acgctgcgcg taaccaccac    5400
acccgccgcg cttaatgcgc cgctacaggg cgcgtcgcgc cattcgccat tcaggctacg    5460
caactgttgg gaagggcgat cggtgcgggc ctcttcgcta ttacgccagg ctgc          5514
```

<210> SEQ ID NO 4
<211> LENGTH: 3421
<212> TYPE: DNA
<213> ORGANISM: Artificial Sequence
<220> FEATURE:

<223> OTHER INFORMATION: Synthetic Polynucleotide

<400> SEQUENCE: 4

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctcagat ctgaattcgg taccctagtt attaatagta     180
atcaattacg gggtcattag ttcatagccc atatatggag ttccgcgtta cataacttac     240
ggtaaatggc ccgcctggct gaccgcccaa cgacccccgc ccattgacgt caataatgac     300
gtatgttccc atagtaacgc caatagggac tttccattga cgtcaatggg tggactattt     360
acggtaaact gcccacttgg cagtacatca agtgtatcat atgccaagta cgccccctat     420
tgacgtcaat gacggtaaat ggcccgcctg gcattatgcc cagtacatga ccttatggga     480
ctttcctact tggcagtaca tctacgtatt agtcatcgct attaccatgg tcgaggtgag     540
ccccacgttc tgcttcactc tccccatctc ccccccctcc ccaccccaa ttttgtattt      600
atttattttt taattatttt gtgcagcgat gggggcgggg ggggggggg gcgcgcgcc       660
aggcggggcg gggcggggcg aggggcgggg cgggcgagg cggagaggtg cggcggcagc      720
caatcagagc ggcgcgctcc gaaagtttcc ttttatggcg aggcggcggc ggcggcggcc     780
ctataaaag cgaagcgcgc ggcgggcggg agtcgctgcg acgctgcctt cgccccgtgc      840
cccgctccgc cgccgcctcg cgccgcccgc cccggctctg actgaccgcg ttactcccac     900
aggtgagcgg gcgggacggc ccttctcctc cgggctgtaa ttagcgcttg gtttaatgac     960
ggcttgtttc ttttctgtgg ctgcgtgaaa gccttgaggg gctccgggag ctagagcctc    1020
tgctaaccat gttcatgcct tcttctttt cctacagctc ctgggcaacg tgctggttat     1080
tgtgctgtct catcattttg gcaaagaatt cctcgaagaa ctaggcaacg cgtctcgagg    1140
ccaccatgaa gtatctggtc ctcgtcttat gtttaacgtc gtgcgcgtgt cgagatatcg    1200
gactatggac gttccgatac gtctacaacg aaagcgacaa cgtcgtgttc tcaccgtacg    1260
gcttgacctc cgcgttgtcc gtgttacgga tcgcggcggg cggtaacacg aaacgagaaa    1320
tagacgtccc cgaatccgtc gtggaggact ccgacgcctt tctcgcgtta cgggagttgt    1380
tcgtagacgc atccgttccg ttacgtcccg agtttacggc ggagttctcc tcgcgattca    1440
atacctccgt gcaacgcgtg acgtttaact cggagaacgt caaagacgtc attaactcgt    1500
acgttaagga taagacggga ggagacgtcc cacgcgtatt ggacgcctcc ctagaccgag    1560
atactaaaat gctgctattg agctccgttc gtatgaagac gagctggaga cacgtattcg    1620
acccttcgtt cacgacggat caacctttt attccggaaa cgtcacatac aaggtacgta     1680
tgatgaataa aatagatacg ttgaaaacgg agacgtttac gcttagaaac gtgggatact    1740
ccgtaacgga actgccgtat aaacggcgtc aaacggccat gttgctcgtc gttccggacg    1800
acttgggaga gatcgtgcgg gccctcgatc tttctctagt acgcttctgg atacgcaaca    1860
tgaggaaaga cgtgtgtcag gtggtaatgc ccaagttctc cgtcgaatcg gtcctggatc    1920
tgagggacgc cctccagaga ctgggggtgc gagacgcgtt cgatccatcc cgggcggact    1980
tcggtcaggt gtcccgtcg aacgatctat acgtcacgaa ggtgttacag acgtccaaga    2040
tagaggcgga cgaacgggga acgacggcgt cgagcgacac agccatcacc ctcatcccca    2100
ggaacgccct cacggcgatc gtggcgaaca aaccgtttat gtttctcatc tatcacaagc    2160
ctacaacgac cgtgttgttt atgggaacga taacaaaggg tgaaaaagta atatacgata    2220
cggagggtcg agatgatgtc gtatcctctg tagcggccgc tgctactaac ttcagcctgc    2280
```

```
tgaagcaggc tggagacgtg gaggagaacc ctggaccttc cggaatgagc aagggcgagg      2340
aactgttcac tggcgtggtc ccaattctcg tggaactgga tggcgatgtg aatgggcaca      2400
aattttctgt cagcggagag ggtgaaggtg atgccacata cggaaagctc accctgaaat      2460
tcatctgcac cactggaaag ctccctgtgc catggccaac actggtcact accctgacct      2520
atggcgtgca gtgcttttcc agatacccag accatatgaa gcagcatgac ttttcaaga      2580 gcgccatgcc cgagggctat gtgcaggaga gaaccatctt tttcaaagat gacgggaact      2640
acaagacccg cgctgaagtc aagttcgaag gtgacaccct ggtgaataga atcgagctga      2700
agggcattga ctttaaggag gatggaaaca ttctcggcca caagctggaa tacaactata      2760
actcccacaa tgtgtacatc atggccgaca gcaaaagaa tggcatcaag gtcaacttca      2820
agatcagaca caacattgag gatggatccg tgcagctggc cgaccattat caacagaaca      2880
ctccaatcgg cgacggccct gtgctcctcc cagacaacca ttacctgtcc acccagtctg      2940
ccctgtctaa agatcccaac gaaaagagag accacatggt cctgctggag tttgtgaccg      3000
ctgctgggat cacacatggc atggacgagc tgtacaagtg aatgcatgcg ccgcgcgga       3060 tccagacatg ataagataca ttgatgagtt tggacaaacc acaactagaa tgcagtgaaa      3120
aaaatgcttt atttgtgaaa tttgtgatgc tattgcttta tttgtaacca ttataagctg      3180
caataaacaa gttaacaaca acaattgcat tcattttatg tttcaggttc aggggggaggt      3240 gtgggaggtt ttttagtcga ctggggagag atctgaggaa cccctagtga tggagttggc      3300
cactccctct ctgcgcgctc gctcgctcac tgaggccgcc cgggcaaagc ccggcgtcg       3360 ggcgacctt ggtcgcccgg cctcagtgag cgagcgagcg cgcagagagg gagtggccaa       3420
c                                                                      3421
```

<210> SEQ ID NO 5
<211> LENGTH: 2635
<212> TYPE: DNA
<213> ORGANISM: Artificial Sequence
<220> FEATURE:
<223> OTHER INFORMATION: Synthetic Polynucleotide

<400> SEQUENCE: 5

```
ttggccactc cctctctgcg cgctcgctcg ctcactgagg ccgggcgacc aaaggtcgcc       60
cgacgcccgg gctttgcccg gcggccctca gtgagcgagc gagcgcgcag agagggagtg      120
gccaactcca tcactagggg ttcctcagat ctgaattcgg taccctagtt attaatagta      180
atcaattacg gggtcattag ttcatagccc atatatggag ttccgcgtta cataacttac      240
ggtaaatggc ccgcctggct gaccgcccaa cgacccccgc ccattgacgt caataatgac      300
gtatgttccc atagtaacgc caatagggac tttccattga cgtcaatggg tggactattt      360
acggtaaact gcccacttgg cagtacatca agtgtatcat atgccaagta cgccccctat      420
tgacgtcaat gacggtaaat ggcccgcctg gcattatgcc cagtacatga ccttatggga      480
ctttcctact tggcagtaca tctacgtatt agtcatcgct attaccatgg tcgaggtgag      540
ccccacgttc tgcttcactc tccccatctc cccccctcc ccaccccaa ttttgtattt        600 atttattttt aattattttt gtgcagcgat ggggcgggg ggggggggg ggcgcgcgcc         660 aggcggggcg gggcgggcg aggggcgggg cggggcgagg cggagaggtg cggcggcagc       720
caatcagagc ggcgcgctcc gaaagtttcc ttttatggcg aggcggcggc ggcggcggcc      780
ctataaaaag cgaagcgcgc ggcgggcggg agtcgctgcg acgctgcctt cgccccgtgc      840
```

```
cccgctccgc cgccgcctcg cgccgcccgc cccggctctg actgaccgcg ttactcccac      900
aggtgagcgg gcgggacggc ccttctcctc cgggctgtaa ttagcgcttg gtttaatgac      960
ggcttgtttc ttttctgtgg ctgcgtgaaa gccttgaggg gctccgggag ctagagcctc     1020
tgctaaccat gttcatgcct tcttcttttt cctacagctc ctgggcaacg tgctggttat     1080
tgtgctgtct catcattttg gcaaagaatt cctcgaagaa ctaggcaacg cgtctcgagg     1140
ccaccatgaa gtatctggtc ctcgtcttat gtttaacgtc gtgcgcgtgt cgagatatcg     1200
gactatggac gttccgatac gtctacaacg aaagcgacaa cgtcgtgttc tcaccgtacg     1260
gcttgacctc cgcgttgtcc gtgttacgga tcgcggcggg cggtaacacg aaacgagaaa     1320
tagacgtccc cgaatccgtc gtggaggact ccgacgcctt tctcgcgtta cgggagttgt     1380
tcgtagacgc atccgttccg ttacgtcccg agtttacggc ggagttctcc tcgcgattca     1440
atacctccgt gcaacgcgtg acgtttaact cggagaacgt caaagacgtc attaactcgt     1500
acgttaagga taagacggga ggagacgtcc cacgcgtatt ggacgcctcc ctagaccgag     1560
atactaaaat gctgctattg agctccgttc gtatgaagac gagctggaga cacgtattcg     1620
acccttcgtt cacgacggat caaccttttt attccggaaa cgtcacatac aaggtacgta     1680
tgatgaataa aatagatacg ttgaaaacgg agacgtttac gcttagaaac gtgggatact     1740
ccgtaacgga actgccgtat aaacggcgtc aaacggccat gttgctcgtc gttccggacg     1800
acttgggaga gatcgtgcgg gccctcgatc tttctctagt acgcttctgg atacgcaaca     1860
tgaggaaaga cgtgtgtcag gtggtaatgc ccaagttctc cgtcgaatcg gtcctggatc     1920
tgagggacgc cctccagaga ctgggggtgc gagacgcgtt cgatccatcc cgggcggact     1980
tcggtcaggc gtccccgtcg aacgatctat acgtcacgaa ggtgttacag acgtccaaga     2040
tagaggcgga cgaacgggga acgacggcgt cgagcgacac agccatcacc ctcatcccca     2100
ggaacgccct cacggcgatc gtggcgaaca aaccgtttat gtttctcatc tatcacaagc     2160
ctacaacgac cgtgttgttt atgggaacga taacaaaggg tgaaaaagta atatacgata     2220
cggagggtcg agatgatgtc gtatcctctg tatgaatgca tgcggccgcg cggatccaga     2280
catgataaga tacattgatg agtttggaca aaccacaact agaatgcagt gaaaaaaatg     2340
ctttatttgt gaaatttgtg atgctattgc tttatttgta accattataa gctgcaataa     2400
acaagttaac aacaacaatt gcattcattt tatgtttcag gttcaggggg aggtgtggga     2460
ggttttttag tcgactgggg agagatctga ggaacccta gtgatggagt tggccactcc     2520
ctctctgcgc gctcgctcgc tcactgaggc cgcccgggca agcccgggc gtcgggcgac      2580
ctttggtcgc ccggcctcag tgagcgagcg agcgcgcaga gagggagtgg ccaac         2635
```

<210> SEQ ID NO 6
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 6

Ala Thr Asn Phe Ser Leu Leu Lys Gln Ala Gly Asp Val Glu Glu Asn
1               5                   10                  15

Pro Gly Pro

<210> SEQ ID NO 7
<211> LENGTH: 5
<212> TYPE: PRT

```
<213> ORGANISM: Artificial Sequence
<220> FEATURE:
<223> OTHER INFORMATION: Synthetic Polypeptide

<400> SEQUENCE: 7

Gly Gly Gly Gly Ser
1               5
```